United States Patent
Burnett, Jr. et al.

(10) Patent No.: US 6,387,655 B1
(45) Date of Patent: May 14, 2002

(54) EXCITATORY AMINO ACID RECEPTOR PROTEIN AND RELATED NUCLEIC ACID COMPOUNDS

(75) Inventors: J. Paul Burnett, Jr.; Nancy Gail Mayne; Robert Leon Sharp, all of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/794,158

(22) Filed: Dec. 19, 1996

Related U.S. Application Data

(60) Provisional application No. 60/008,959, filed on Dec. 20, 1995.

(51) Int. Cl.[7] ........................ C07K 14/705; C12N 15/12
(52) U.S. Cl. ................ 435/69.1; 435/252.3; 435/320.1; 530/350; 536/23.5
(58) Field of Search ............................. 435/69.1, 6, 7.1, 435/7.2, 252.3, 320.1; 530/350; 536/23.5

(56) References Cited

U.S. PATENT DOCUMENTS 5,521,297 A * 5/1996 Daggett et al. ............ 536/23.5

OTHER PUBLICATIONS

Amara, S.G., "A tale of two families", *Nature* 360:420–421, Dec. 3, 1992.*

Yasuto Tanabe et al. "A Family of Metabotropic Glutamate Receptors" *Neuron* 8:169–179 (Jan., 1992).

* cited by examiner

*Primary Examiner*—John Ulm
(74) *Attorney, Agent, or Firm*—Alexander Wilson; Thomas D. Webster

(57) ABSTRACT

This invention describes a novel human glutamate receptors, designated HmGluR3. This invention also encompasses nucleic acids encoding this receptor, or a fragment thereof, as well as methods employing this receptor and the nucleic acid compounds.

18 Claims, 2 Drawing Sheets

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
       (A) LENGTH: 2637 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (ix) FEATURE:
       (A) NAME/KEY: CDS
       (B) LOCATION: 1..2637

(xi) SEQUENCE DESCRIPTION: SEQ ID NO:1:

```
ATG AAG ATG TTG ACA AGA CTG CAA GTT CTT ACC TTA GCT TTG TTT TCA      48
Met Lys Met Leu Thr Arg Leu Gln Val Leu Thr Leu Ala Leu Phe Ser
 1               5                  10                  15

AAG GGA TTT TTA CTC TCT TTA GGG GAC CAT AAC TTT CTA AGG AGA GAG      96
Lys Gly Phe Leu Leu Ser Leu Gly Asp His Asn Phe Leu Arg Arg Glu
             20                  25                  30

ATT AAA ATA GAA GGT GAC CTT GTT TTA GGG GGC CTG TTT CCT ATT AAC     144
Ile Lys Ile Glu Gly Asp Leu Val Leu Gly Gly Leu Phe Pro Ile Asn
         35                  40                  45

GAA AAA GGC ACT GGA ACT GAA GAA TGT GGG CGA ATC AAT GAA GAC CGA     192
Glu Lys Gly Thr Gly Thr Glu Glu Cys Gly Arg Ile Asn Glu Asp Arg
     50                  55                  60

GGG ATT CAA CGC CTG GAA GCC ATG TTG TTT GCT ATT GAT GAA ATC AAC     240
Gly Ile Gln Arg Leu Glu Ala Met Leu Phe Ala Ile Asp Glu Ile Asn
 65                  70                  75                  80

AAA GAT GAT TAC TTG CTA CCA GGA GTG AAG TTG GGT GTT CAC ATT TTG     288
Lys Asp Asp Tyr Leu Leu Pro Gly Val Lys Leu Gly Val His Ile Leu
                 85                  90                  95

GAT ACA TGT TCA AGG GAT ACC TAT GCA TTG GAG CAA TCA CTG GAG TTT     336
Asp Thr Cys Ser Arg Asp Thr Tyr Ala Leu Glu Gln Ser Leu Glu Phe
            100                 105                 110

GTC AGG GCA TCT TTG ACA AAA GTG GAT GAA GCT GAG TAT ATG TGT CCT     384
Val Arg Ala Ser Leu Thr Lys Val Asp Glu Ala Glu Tyr Met Cys Pro
        115                 120                 125

GAT GGA TCC TAT GCC ATT CAA GAA AAC ATC CCA CTT CTC ATT GCA GGG     432
Asp Gly Ser Tyr Ala Ile Gln Glu Asn Ile Pro Leu Leu Ile Ala Gly
    130                 135                 140

GTC ATT GGT GGC TCT TAT AGC AGT GTT TCC ATA CAG GTG GCA AAC CTG     480
Val Ile Gly Gly Ser Tyr Ser Ser Val Ser Ile Gln Val Ala Asn Leu
145                 150                 155                 160

CTG CGG CTC TTC CAG ATC CCT CAG ATC AGC TAC GCA TCC ACC AGC GCC     528
Leu Arg Leu Phe Gln Ile Pro Gln Ile Ser Tyr Ala Ser Thr Ser Ala
                165                 170                 175

AAA CTC AGT GAT AAG TCG CGC TAT GAT TAC TTT GCC AGG ACC GTG CCC     576
Lys Leu Ser Asp Lys Ser Arg Tyr Asp Tyr Phe Ala Arg Thr Val Pro
            180                 185                 190

CCC GAC TTC TAC CAG GCC AAA GCC ATG GCT GAG ATC TTG CGC TTC TTC     624
Pro Asp Phe Tyr Gln Ala Lys Ala Met Ala Glu Ile Leu Arg Phe Phe
        195                 200                 205
```

```
AAC TGG ACC TAC GTG TCC ACA GTA GCC TCC GAG GGT GAT TAC GGG GAG      672
Asn Trp Thr Tyr Val Ser Thr Val Ala Ser Glu Gly Asp Tyr Gly Glu
    210             215             220

ACA GGG ATC GAG GCC TTC GAG CAG GAA GCC CGC CTG CGC AAC ATC TGC      720
Thr Gly Ile Glu Ala Phe Glu Gln Glu Ala Arg Leu Arg Asn Ile Cys
225             230             235             240

ATC GCT ACG GCG GAG AAG GTG GGC CGC TCC AAC ATC CGC AAG TCC TAC      768
Ile Ala Thr Ala Glu Lys Val Gly Arg Ser Asn Ile Arg Lys Ser Tyr
                245             250             255

GAC AGC GTG ATC CGA GAA CTG TTG CAG AAG CCC AAC GCG CGC GTC GTG      816
Asp Ser Val Ile Arg Glu Leu Leu Gln Lys Pro Asn Ala Arg Val Val
            260             265             270

GTC CTC TTC ATG CGC AGC GAC GAC TCG CGG GAG CTC ATT GCA GCC GCC      864
Val Leu Phe Met Arg Ser Asp Asp Ser Arg Glu Leu Ile Ala Ala Ala
        275             280             285

AGC CGC GCC AAT GCC TCC TTC ACC TGG GTG GCC AGC GAC GGC TGG GGC      912
Ser Arg Ala Asn Ala Ser Phe Thr Trp Val Ala Ser Asp Gly Trp Gly
    290             295             300

GCG CAG GAG AGC ATC ATC AAG GGC AGC GAG CAT GTG GCC TAC GGC GCC      960
Ala Gln Glu Ser Ile Ile Lys Gly Ser Glu His Val Ala Tyr Gly Ala
305             310             315             320

ATC ACC CTG GAG CTG GCC TCC CAG CCT GTC CGC CAG TTC GAC CGC TAC     1008
Ile Thr Leu Glu Leu Ala Ser Gln Pro Val Arg Gln Phe Asp Arg Tyr
                325             330             335

TTC CAG AGC CTC AAC CCC TAC AAC AAC CAC CGC AAC CCC TGG TTC CGG     1056
Phe Gln Ser Leu Asn Pro Tyr Asn Asn His Arg Asn Pro Trp Phe Arg
            340             345             350

GAC TTC TGG GAG CAA AAG TTT CAG TGC AGC CTC CAG AAC AAA CGC AAC     1104
Asp Phe Trp Glu Gln Lys Phe Gln Cys Ser Leu Gln Asn Lys Arg Asn
        355             360             365

CAC AGG CGC GTC TGC GAC AAG CAC CTG GCC ATC GAC AGC AGC AAC TAC     1152
His Arg Arg Val Cys Asp Lys His Leu Ala Ile Asp Ser Ser Asn Tyr
    370             375             380

GAG CAA GAG TCC AAG ATC ATG TTT GTG GTG AAC GCG GTG TAT GCC ATG     1200
Glu Gln Glu Ser Lys Ile Met Phe Val Val Asn Ala Val Tyr Ala Met
385             390             395             400

GCC CAC GCT TTG CAC AAA ATG CAG CGC ACC CTC TGT CCC AAC ACT ACC     1248
Ala His Ala Leu His Lys Met Gln Arg Thr Leu Cys Pro Asn Thr Thr
                405             410             415

AAG CTT TGT GAT GCT ATG AAG ATC CTG GAT GGG AAG AAG TTG TAC AAG     1296
Lys Leu Cys Asp Ala Met Lys Ile Leu Asp Gly Lys Lys Leu Tyr Lys
            420             425             430

GAT TAC TTG CTG AAA ATC AAC TTC ACG GCT CCA TTC AAC CCA AAT AAA     1344
Asp Tyr Leu Leu Lys Ile Asn Phe Thr Ala Pro Phe Asn Pro Asn Lys
        435             440             445

GAT GCA GAT AGC ATA GTC AAG TTT GAC ACT TTT GGA GAT GGA ATG GGG     1392
Asp Ala Asp Ser Ile Val Lys Phe Asp Thr Phe Gly Asp Gly Met Gly
    450             455             460

CGA TAC AAC GTG TTC AAT TTC CAA AAT GTA GGT GGA AAG TAT TCC TAC     1440
Arg Tyr Asn Val Phe Asn Phe Gln Asn Val Gly Gly Lys Tyr Ser Tyr
465             470             475             480

TTG AAA GTT GGT CAC TGG GCA GAA ACC TTA TCG CTA GAT GTC AAC TCT     1488
Leu Lys Val Gly His Trp Ala Glu Thr Leu Ser Leu Asp Val Asn Ser
                485             490             495

ATC CAC TGG TCC CGG AAC TCA GTC CCC ACT TCC CAG TGC AGC GAC CCC     1536
Ile His Trp Ser Arg Asn Ser Val Pro Thr Ser Gln Cys Ser Asp Pro
            500             505             510

TGT GCC CCC AAT GAA ATG AAG AAT ATG CAA CCA GGG GAT GTC TGC TGC     1584
Cys Ala Pro Asn Glu Met Lys Asn Met Gln Pro Gly Asp Val Cys Cys
```

```
                    -continued 515                520                525
TGG ATT TGC ATC CCC TGT GAA CCC TAC GAA TAC CTG GCT GAT GAG TTT    1632
Trp Ile Cys Ile Pro Cys Glu Pro Tyr Glu Tyr Leu Ala Asp Glu Phe
        530                535                540

ACC TGT ATG GAT TGT GGG TCT GGA CAG TGG CCC ACT GCA GAC CTA ACT    1680
Thr Cys Met Asp Cys Gly Ser Gly Gln Trp Pro Thr Ala Asp Leu Thr
545                550                555                560

GGA TGC TAT GAC CTT CCT GAG GAC TAC ATC AGG TGG GAA GAC GCC TGG    1728
Gly Cys Tyr Asp Leu Pro Glu Asp Tyr Ile Arg Trp Glu Asp Ala Trp
                565                570                575

GCC ATT GGC CCA GTC ACC ATT GCC TGT CTG GGT TTT ATG TGT ACA TGC    1776
Ala Ile Gly Pro Val Thr Ile Ala Cys Leu Gly Phe Met Cys Thr Cys
        580                585                590

ATG GTT GTA ACT GTT TTT ATC AAG CAC AAC AAC ACA CCC TTG GTC AAA    1824
Met Val Val Thr Val Phe Ile Lys His Asn Asn Thr Pro Leu Val Lys
            595                600                605

GCA TCG GGC CGA GAA CTC TGC TAC ATC TTA TTG TTT GGG GTT GGC CTG    1872
Ala Ser Gly Arg Glu Leu Cys Tyr Ile Leu Leu Phe Gly Val Gly Leu
        610                615                620

TCA TAC TGC ATG ACA TTC TTC TTC ATT GCC AAG CCA TCA CCA GTC ATC    1920
Ser Tyr Cys Met Thr Phe Phe Phe Ile Ala Lys Pro Ser Pro Val Ile
625                630                635                640

TGT GCA TTG CGC CGA CTC GGG CTG GGG AGT TCC TTC GCT ATC TGT TAC    1968
Cys Ala Leu Arg Arg Leu Gly Leu Gly Ser Ser Phe Ala Ile Cys Tyr
                645                650                655

TCA GCC CTG CTG ACC AAG ACA AAC TGC ATT GCC CGC ATC TTC GAT GGG    2016
Ser Ala Leu Leu Thr Lys Thr Asn Cys Ile Ala Arg Ile Phe Asp Gly
        660                665                670

GTC AAG AAT GGC GCT CAG AGG CCA AAA TTC ATC AGC CCC AGT TCT CAG    2064
Val Lys Asn Gly Ala Gln Arg Pro Lys Phe Ile Ser Pro Ser Ser Gln
            675                680                685

GTT TTC ATC TGC CTG GGT CTG ATC CTG GTG CAA ATT GTG ATG GTG TCT    2112
Val Phe Ile Cys Leu Gly Leu Ile Leu Val Gln Ile Val Met Val Ser
        690                695                700

GTG TGG CTC ATC CTG GAG GCC CCA GGC ACC AGG AGG TAT ACC CTT GCA    2160
Val Trp Leu Ile Leu Glu Ala Pro Gly Thr Arg Arg Tyr Thr Leu Ala
705                710                715                720

GAG AAG CGG GAA ACA GTC ATC CTA AAA TGC AAT GTC AAA GAT TCC AGC    2208
Glu Lys Arg Glu Thr Val Ile Leu Lys Cys Asn Val Lys Asp Ser Ser
                725                730                735

ATG TTG ATC TCT CTT ACC TAC GAT GTG ATC CTG GTG ATC TTA TGC ACT    2256
Met Leu Ile Ser Leu Thr Tyr Asp Val Ile Leu Val Ile Leu Cys Thr
        740                745                750

GTG TAC GCC TTC AAA ACG CGG AAG TGC CCA GAA AAT TTC AAC GAA GCT    2304
Val Tyr Ala Phe Lys Thr Arg Lys Cys Pro Glu Asn Phe Asn Glu Ala
            755                760                765

AAG TTC ATA GGT TTT ACC ATG TAC ACC ACG TGC ATC ATC TGG TTG GCC    2352
Lys Phe Ile Gly Phe Thr Met Tyr Thr Thr Cys Ile Ile Trp Leu Ala
        770                775                780

TTC CTC CCT ATA TTT TAT GTG ACA TCA AGT GAC TAC AGA GTG CAG ACG    2400
Phe Leu Pro Ile Phe Tyr Val Thr Ser Ser Asp Tyr Arg Val Gln Thr
785                790                795                800

ACA ACC ATG TGC ATC TCT GTC AGC CTG AGT GGC TTT GTG GTC TTG GGC    2448
Thr Thr Met Cys Ile Ser Val Ser Leu Ser Gly Phe Val Val Leu Gly
                805                810                815

TGT TTG TTT GCA CCC AAG GTT CAC ATC ATC CTG TTT CAA CCC CAG AAG    2496
Cys Leu Phe Ala Pro Lys Val His Ile Ile Leu Phe Gln Pro Gln Lys
        820                825                830

AAT GTT GTC ACA CAC AGA CTG CAC CTC AAC AGG TTC AGT GTC AGT GGA    2544
```

```
Asn Val Val Thr His Arg Leu His Leu Asn Arg Phe Ser Val Ser Gly
            835                 840                 845

ACT GGG ACC ACA TAC TCT CAG TCC TCT GCA AGC ACG TAT GTG CCA ACG       2592
Thr Gly Thr Thr Tyr Ser Gln Ser Ser Ala Ser Thr Tyr Val Pro Thr
    850                 855                 860

GTG TGC AAT GGG CGG GAA GTC CTC GAC TCC ACC ACC TCA TCT CTG           2637
Val Cys Asn Gly Arg Glu Val Leu Asp Ser Thr Thr Ser Ser Leu
865             870                 875
```

(2) INFORMATION FOR SEQ ID NO:2:

(i) SEQUENCE CHARACTERISTICS:
      (A) LENGTH: 879 amino acids
      (B) TYPE: amino acid
      (D) TOPOLOGY: linear (ii) MOLECULE TYPE: protein (xi) SEQUENCE DESCRIPTION: SEQ ID NO:2:

```
Met Lys Met Leu Thr Arg Leu Gln Val Leu Thr Leu Ala Leu Phe Ser
1               5                   10                  15

Lys Gly Phe Leu Leu Ser Leu Gly Asp His Asn Phe Leu Arg Arg Glu
            20                  25                  30

Ile Lys Ile Glu Gly Asp Leu Val Leu Gly Gly Leu Phe Pro Ile Asn
        35                  40                  45

Glu Lys Gly Thr Gly Thr Glu Glu Cys Gly Arg Ile Asn Glu Asp Arg
    50                  55                  60

Gly Ile Gln Arg Leu Glu Ala Met Leu Phe Ala Ile Asp Glu Ile Asn
65                  70                  75                  80

Lys Asp Asp Tyr Leu Leu Pro Gly Val Lys Leu Gly Val His Ile Leu
                85                  90                  95

Asp Thr Cys Ser Arg Asp Thr Tyr Ala Leu Glu Gln Ser Leu Glu Phe
            100                 105                 110

Val Arg Ala Ser Leu Thr Lys Val Asp Glu Ala Glu Tyr Met Cys Pro
        115                 120                 125

Asp Gly Ser Tyr Ala Ile Gln Glu Asn Ile Pro Leu Leu Ile Ala Gly
    130                 135                 140

Val Ile Gly Gly Ser Tyr Ser Ser Val Ser Ile Gln Val Ala Asn Leu
145                 150                 155                 160

Leu Arg Leu Phe Gln Ile Pro Gln Ile Ser Tyr Ala Ser Thr Ser Ala
                165                 170                 175

Lys Leu Ser Asp Lys Ser Arg Tyr Asp Tyr Phe Ala Arg Thr Val Pro
            180                 185                 190

Pro Asp Phe Tyr Gln Ala Lys Ala Met Ala Glu Ile Leu Arg Phe Phe
        195                 200                 205

Asn Trp Thr Tyr Val Ser Thr Val Ala Ser Glu Gly Asp Tyr Gly Glu
    210                 215                 220

Thr Gly Ile Glu Ala Phe Glu Gln Glu Ala Arg Leu Arg Asn Ile Cys
225                 230                 235                 240

Ile Ala Thr Ala Glu Lys Val Gly Arg Ser Asn Ile Arg Lys Ser Tyr
                245                 250                 255

Asp Ser Val Ile Arg Glu Leu Leu Gln Lys Pro Asn Ala Arg Val Val
            260                 265                 270

Val Leu Phe Met Arg Ser Asp Asp Ser Arg Glu Leu Ile Ala Ala Ala
        275                 280                 285

Ser Arg Ala Asn Ala Ser Phe Thr Trp Val Ala Ser Asp Gly Trp Gly
    290                 295                 300
```

-continued

```
Ala Gln Glu Ser Ile Ile Lys Gly Ser Glu His Val Ala Tyr Gly Ala
305                 310                 315                 320

Ile Thr Leu Glu Leu Ala Ser Gln Pro Val Arg Gln Phe Asp Arg Tyr
            325                 330                 335

Phe Gln Ser Leu Asn Pro Tyr Asn Asn His Arg Asn Pro Trp Phe Arg
            340                 345                 350

Asp Phe Trp Glu Gln Lys Phe Gln Cys Ser Leu Gln Asn Lys Arg Asn
            355                 360                 365

His Arg Arg Val Cys Asp Lys His Leu Ala Ile Asp Ser Ser Asn Tyr
370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
            405                 410                 415

Lys Leu Cys Asp Ala Met Lys Ile Leu Asp Gly Lys Lys Leu Tyr Lys
            420                 425                 430

Asp Tyr Leu Leu Lys Ile Asn Phe Thr Ala Pro Phe Asn Pro Asn Lys
            435                 440                 445

Asp Ala Asp Ser Ile Val Lys Phe Asp Thr Phe Gly Asp Gly Met Gly
450                 455                 460

Arg Tyr Asn Val Phe Asn Phe Gln Asn Val Gly Gly Lys Tyr Ser Tyr
465                 470                 475                 480

Leu Lys Val Gly His Trp Ala Glu Thr Leu Ser Leu Asp Val Asn Ser
            485                 490                 495

Ile His Trp Ser Arg Asn Ser Val Pro Thr Ser Gln Cys Ser Asp Pro
            500                 505                 510

Cys Ala Pro Asn Glu Met Lys Asn Met Gln Pro Gly Asp Val Cys Cys
            515                 520                 525

Trp Ile Cys Ile Pro Cys Glu Pro Tyr Glu Tyr Leu Ala Asp Glu Phe
            530                 535                 540

Thr Cys Met Asp Cys Gly Ser Gly Gln Trp Pro Thr Ala Asp Leu Thr
545                 550                 555                 560

Gly Cys Tyr Asp Leu Pro Glu Asp Tyr Ile Arg Trp Glu Asp Ala Trp
            565                 570                 575

Ala Ile Gly Pro Val Thr Ile Ala Cys Leu Gly Phe Met Cys Thr Cys
            580                 585                 590

Met Val Val Thr Val Phe Ile Lys His Asn Asn Thr Pro Leu Val Lys
            595                 600                 605

Ala Ser Gly Arg Glu Leu Cys Tyr Ile Leu Leu Phe Gly Val Gly Leu
610                 615                 620

Ser Tyr Cys Met Thr Phe Phe Ile Ala Lys Pro Ser Pro Val Ile
625                 630                 635                 640

Cys Ala Leu Arg Arg Leu Gly Leu Gly Ser Ser Phe Ala Ile Cys Tyr
            645                 650                 655

Ser Ala Leu Leu Thr Lys Thr Asn Cys Ile Ala Arg Ile Phe Asp Gly
            660                 665                 670

Val Lys Asn Gly Ala Gln Arg Pro Lys Phe Ile Ser Pro Ser Ser Gln
            675                 680                 685

Val Phe Ile Cys Leu Gly Leu Ile Leu Val Gln Ile Val Met Val Ser
            690                 695                 700

Val Trp Leu Ile Leu Glu Ala Pro Gly Thr Arg Arg Tyr Thr Leu Ala
705                 710                 715                 720
```

-continued

```
Glu Lys Arg Glu Thr Val Ile Leu Lys Cys Asn Val Lys Asp Ser Ser
            725                 730                 735
Met Leu Ile Ser Leu Thr Tyr Asp Val Ile Leu Val Ile Leu Cys Thr
            740                 745                 750
Val Tyr Ala Phe Lys Thr Arg Lys Cys Pro Glu Asn Phe Asn Glu Ala
            755                 760                 765
Lys Phe Ile Gly Phe Thr Met Tyr Thr Thr Cys Ile Ile Trp Leu Ala
            770                 775                 780
Phe Leu Pro Ile Phe Tyr Val Thr Ser Ser Asp Tyr Arg Val Gln Thr
785                 790                 795                 800
Thr Thr Met Cys Ile Ser Val Ser Leu Ser Gly Phe Val Val Leu Gly
            805                 810                 815
Cys Leu Phe Ala Pro Lys Val His Ile Ile Leu Phe Gln Pro Gln Lys
            820                 825                 830
Asn Val Val Thr His Arg Leu His Leu Asn Arg Phe Ser Val Ser Gly
            835                 840                 845
Thr Gly Thr Thr Tyr Ser Gln Ser Ser Ala Ser Thr Tyr Val Pro Thr
            850                 855                 860
Val Cys Asn Gly Arg Glu Val Leu Asp Ser Thr Thr Ser Ser Leu
865                 870                 875
```

(2) INFORMATION FOR SEQ ID NO:3:

(i) SEQUENCE CHARACTERISTICS:
        (A) LENGTH: 2637 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

```
AUGAAGAUGU UGACAAGACU GCAAGUUCUU ACCUUAGCUU UGUUUUCAAA GGGAUUUUUA      60
CUCUCUUUAG GGACCAUAAC CUUUCUAAGG AGAGAGAUUA AAAUAGAAGG UGACCUUGUU     120
UUAGGGGGCC UGUUUCCUAU UAACGAAAAA GGCACUGGAA CUGAAGAAUG UGGGCGAAUC     180
AAUGAAGACC GAGGGAUUCA ACGCCUGGAA GCCAUGUUGU UUGCUAUUGA UGAAAUCAAC     240
AAAGAUGAUU ACUUGCUACC AGGAGUGAAG UUGGGUGUUC ACAUUUUGGA UACAUGUUCA     300
AGGGAUACCU AUGCAUUGGA GCAAUCACUG GAGUUUGUCA GGGCAUCUUU GACAAAAGUG     360
GAUGAAGCUG AGUAUAUGUG UCCUGAUGGA UCCUAUGCCA UUCAAGAAAA CAUCCCACUU     420
CUCAUUGCAG GGUCAUUGG UGGCUCUUAU AGCAGUGUUU CCAUACAGGU GGCAAACCUG     480
CUGCGGCUCU UCCAGAUCCC UCAGAUCAGC UACGCAUCCA CCAGCGCCAA ACUCAGUGAU     540
AAGUCGCGCU AUGAUUACUU UGCCAGGACC GUGCCCCCG ACUUCUACCA GGCCAAAGCC     600
AUGGCUGAGA UCUUGCGCUU CUUCAACUGG ACCUACGUGU CCACAGUAGC CUCCGAGGGU     660
GAUUACGGGG AGACAGGGAU CGAGGCCUUC GAGCAGGAAG CCCGCCUGCG CAACAUCUGC     720
AUCGCUACGG CGGAGAAGGU GGGCCGCUCC AACAUCCGCA AGUCCUACGA CAGCGUGAUC     780
CGAGAACUGU UGCAGAAGCC CAACGCGCGC GUCGUGGUCC UCUUCAUGCG CAGCGACGAC     840
UCGCGGGAGC UCAUUGCAGC CGCCAGCCGC GCCAAUGCCU CCUUCACCUG GGUGGCCAGC     900
GACGGCUGGG GCGCGCAGGA GAGCAUCAUC AAGGGCAGCG AGCAUGUGGC CUACGGCGCC     960
```

-continued

```
AUCACCCUGG AGCUGGCCUC CCAGCCUGUC CGCCAGUUCG ACCGCUACUU CCAGAGCCUC    1020

AACCCCUACA ACAACCACCG CAACCCCUGG UUCCGGGACU UCUGGGAGCA AAAGUUCAG     1080

UGCAGCCUCC AGAACAAACG CAACCACAGG CGCGUCUGCG ACAAGCACCU GGCCAUCGAC    1140

AGCAGCAACU ACGAGCAAGA GUCCAAGAUC AUGUUUGUGG UGAACGCGGU GUAUGCCAUG    1200

GCCCACGCUU UGCACAAAAU GCAGCGCACC CUCUGUCCCA ACACUACCAA GCUUUGUGAU    1260

GCUAUGAAGA UCCUGGAUGG GAAGAAGUUG UACAAGGAUU ACUUGCUGAA AAUCAACUUC    1320

ACGGCUCCAU UCAACCCAAA UAAAGAUGCA GAUAGCAUAG UCAAGUUUGA CACUUUUGGA    1380

GAUGGAAUGG GGCGAUACAA CGUGUUCAAU UUCCAAAAUG UAGGUGGAAA GUAUUCCUAC    1440

UUGAAAGUUG GUCACGGGGC AGAAACCUUA UCGCUAGAUG UCAACUCUAU CCACUGGUCC    1500

CGGAACUCAG UCCCCACUUC CCAGUGCAGC GACCCCUGUG CCCCCAAUGA AAUGAAGAAU    1560

AUGCAACCAG GGGAUGUCUG CUGCUGGAUU UGCAUCCCCU GUGAACCCUA CGAAUACCUG    1620

GCUGAUGAGU UUACCUGUAU GGAUUGUGGG UCUGGACAGU GGCCCACUGC AGACCUAACU    1680

GGAUGCUAUG ACCUUCCUGA GGACUACAUC AGGUGGGAAG ACGCCUGGGC CAUUGCCCA     1740

GUCACCAUUG CCUGUCUGGG UUUUAUGUGU ACAUGCAUGG UUGUAACUGU UUUUAUCAAG    1800

CACAACAACA CACCCUUGGU CAAAGCAUCG GGCCGAGAAC UCUGCUACAU CUUAUUGUUU    1860

GGGGUUGGCC UGUCAUACUG CAUGACAUUC UUCUUCAUUG CCAAGCCAUC ACCAGUCAUC    1920

UGUGCAUUGC GCCGACUCGG GCUGGGGAGU UCCUUCGCUA UCUGUUACUC AGCCCUGCUG    1980

ACCAAGACAA ACUGCAUUGC CCGCAUCUUC GAUGGGGUCA AGAAUGGCGC UCAGAGGCCA    2040

AAAUUCAUCA GCCCCAGUUC UCAGGUUUUC AUCUGCCUGG GUCUGAUCCU GGUGCAAAUU    2100

GUGAUGGUGU CUGUGUGGCU CAUCCUGGAG GCCCCAGGCA CCAGGAGGUA UACCCUUGCA    2160

GAGAAGCGGG AAACAGUCAU CCUAAAAAUGC AAUGUCAAAG AUUCCAGCAU GUUGAUCUCU   2220

CUUACCUACG AUGUGAUCCU GGUGAUCUUA UGCACGUGU ACGCCUUCAA AACGCGGAAG     2280

UGCCCAGAAA AUUUCAACGA AGCUAAGUUC AUAGGUUUUA CCAUGUACAC CACGUGCAUC    2340

AUCUGGUUGG CCUUCCUCCC UAUAUUUUAU GUGACAUCAA GUGACUACAG AGUGCAGACG    2400

ACAACCAUGU GCAUCUCUGU CAGCCUGAGU GGCUUUGUGG UCUUGGGCUG UUUGUUUGCA    2460

CCCAAGGUUC ACAUCAUCCU GUUUCAACCC CAGAAGAAUG UUGUCACACA CAGACUGCAC    2520

CUCAACAGGU UCAGUGUCAG UGGAACUGGG ACCACAUACU CUCAGUCCUC UGCAAGCACG    2580

UAUGUGCCAA CGGUGUGCAA UGGGCGGGAA GUCCUCGACU CCACCACCUC AUCUCUG      2637
```

EXCITATORY AMINO ACID RECEPTOR PROTEIN AND RELATED NUCLEIC ACID COMPOUNDS

This application claims benefit under Title 35, United States Code, § 119(e) of U.S. provisional patent application No. 60/008,959, filed Dec. 20, 1995.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Annual Reviews in Pharmacology and Toxicology*, 21:165 (1981); Monaghan, Bridges, and Cotman, *Annual Reviews in Pharmacology and Toxicology*, 29:365 (1989); Watkins, Krogsgaard-Larsen, and Honore, *Transactions in Pharmaceutical Science*, 11:25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, or changes in ion channel function. Schoepp and Conn, *Trends in Pharmacological Science*, 14:13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacological Science*, 11:508 (1990); McDonald and Johnson, *Brain Research Reviews*, 15:41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Agonists and antagonists of these receptors may be useful for the treatment of acute and chronic neurodegenerative conditions, and as antipsychotic, anticonvulsant, analgesic, anxiolytic, antidepressant, and anti-emetic agents.

The present invention provides an additional human excitatory amino acid receptor, designated HmGluR3, to those previously known. The characterization and treatment of physiological disorders is hereby furthered.

SUMMARY OF THE INVENTION

The present invention provides an isolated amino acid compound useful as a human metabotropic glutamate receptor, said compound having the amino acid sequence designated as SEQ ID NO:2.

The invention also provides an isolated nucleic acid compound that comprises a nucleic acid sequence which encodes for the amino acid compounds provided. More particularly, this invention provides the isolated nucleic acid compound having the sequence designated as SEQ ID NO:1.

This invention also provides recombinant nucleic acid vectors comprising nucleic acids encoding SEQ ID NO:2. This invention also encompasses recombinant DNA vectors which comprise the isolated DNA sequence which is SEQ ID NO:1.

The present invention also provides assays for determining the efficacy and reaction profile of agents useful in the treatment or prevention of disorders associated with an excess or deficiency in the amount of glutamate present.

DETAILED DESCRIPTION OF THE INVENTION

Figure 1:
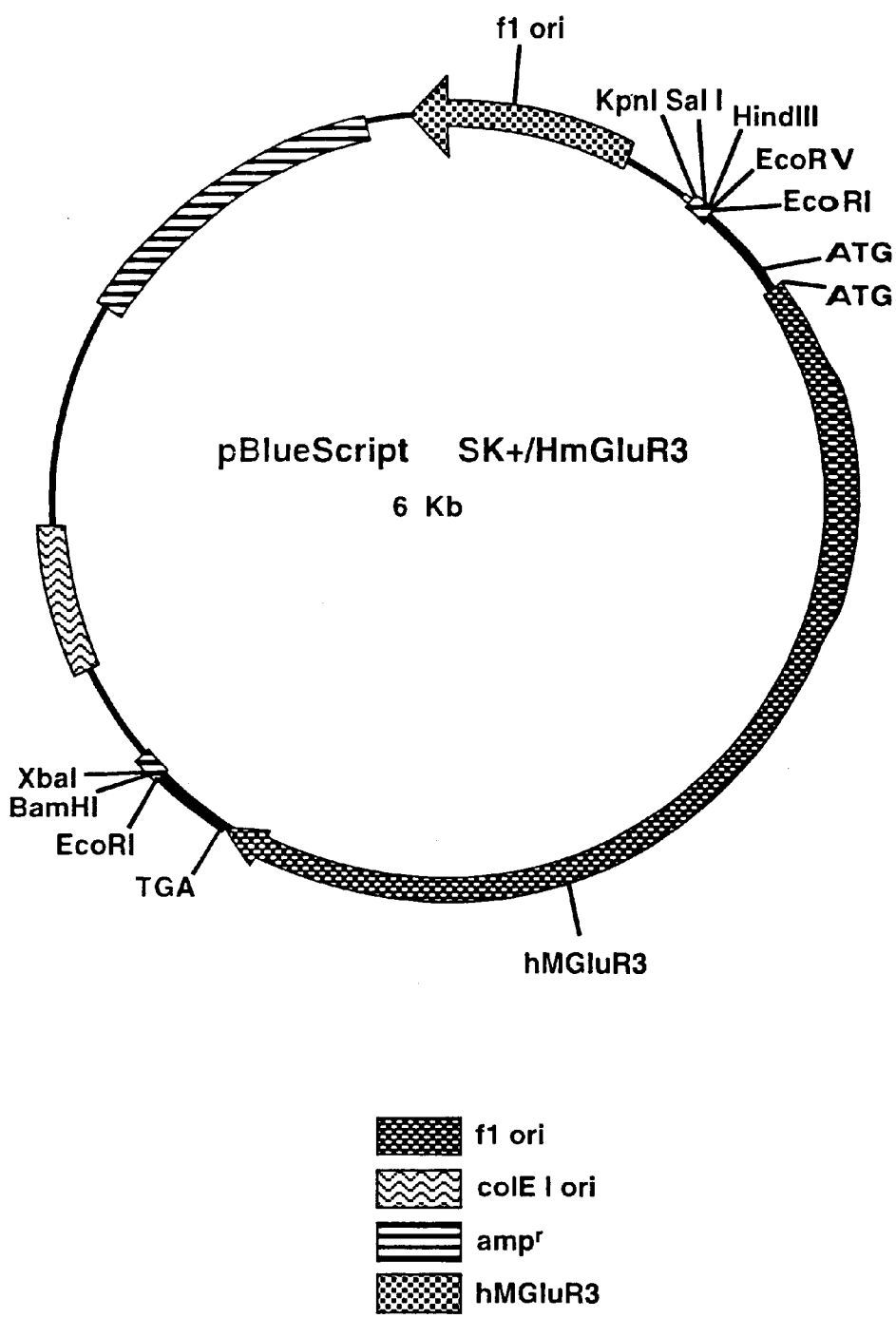
FIG. 1 is a restriction and function map plasmid of pBlueScript®–SK+/HmGluR3. The largest arc indicates that portion of the plasmid which corresponds to SEQ ID NO:1. The arrow delineates that region of the insert which encodes the protein of SEQ ID NO:2 with the direction of the arrow indicating the natural order of transcription from the 5' end to the 3' end. The designation "f1 Ori" refers to the phage origin of replication. The designation "colE 1 Ori" refers to the plasmid origin of replication. The designation "amp$^r$" refers to the gene encoding ampicillin resistance.

The terms and abbreviations used in this document have their normal meanings unless otherwise designated. For example "° C." refers to degrees Celsius; "N" refers to normal or normality; "mmol" refers to millimole or millimoles; "g" refers to gram or grams; "ml" means milliliter or milliliters; "M" refers to molar or molarity; "$\mu$g" refers to microgram or micrograms; and "$\mu$l" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenosine, (deoxy)cytidine, (deoxy)guanosine, and (deoxy)thymidine, respectively, when they occur in DNA molecules. The abbreviations U,C,G, and A correspond to the 5'-monophosphate forms of the ribonucleosides urodine, cytidine, guanosine, and adenosine, respectively when they occur in RNA molecules. In double stranded DNA, base pair may refer to a pairing of A with T or C with G. In a DNA/RNA, heteroduplex base pair may refer to a pairing of A with U or C with G. (See the definition of "complementary", infra.)

The terms "cleavage" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two nucleic acid fragments (T. Maniatis, et al., supra., p. 146). Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A frameshift mutation occurs when a base pair is inserted or deleted from a DNA segment. When this occurs, the result is a different protein from that coded for by the DNA segment prior to the frameshift mutation. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter and other regulatory elements to control transcription of the inserted DNA.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods are summarized in J. Sambrook, et al., "Molecular Cloning: A Laboratory Manual" (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells with polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by joining DNA molecules from different sources. The term "vector" as used herein includes Recombinant DNA cloning vectors and Recombinant DNA expression vectors.

The terms "complementary" or "complementarity" as used herein refers to the pairing of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid hybridization with another nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other glutamate receptor subtypes. This term may also be employed in the sense that such antibodies may be used to differentiate between the human mGluR3 receptor protein and analogous proteins derived from other species.

The term "PCR" as used herein refers to the widely-known polymerase chain reaction employing a thermally-stable polymerase.

The present invention provides an isolated amino acid compound useful as a human metabotropic glutamate receptor, said compound comprising the amino acid sequence:

```
Met Lys Met Leu Thr Arg Leu Gln Val Leu Thr Leu Ala Leu Phe Ser
 1           5                  10                 15
Lys Gly Phe Leu Leu Ser Leu Gly Asp His Asn Phe Leu Arg Arg Glu
            20                  25                 30
Ile Lys Ile Glu Gly Asp Leu Val Leu Gly Gly Leu Phe Pro Ile Asn
        35                  40                 45
Glu Lys Gly Thr Gly Thr Glu Glu Cys Gly Arg Ile Asn Glu Asp Arg
        50                  55                 60
Gly Ile Gln Arg Leu Glu Ala Met Leu Phe Ala Ile Asp Glu Ile Asn
 65                 70                  75                  80
Lys Asp Asp Tyr Leu Leu Pro Gly Val Lys Leu Gly Val His Ile Leu
                85                  90                 95
Asp Thr Cys Ser Arg Asp Thr Tyr Ala Leu Glu Gln Ser Leu Glu Phe
            100                 105                110
Val Arg Ala Ser Leu Thr Lys Val Asp Glu Ala Glu Tyr Met Cys Pro
            115                 120                125
Asp Gly Ser Tyr Ala Ile Gln Glu Asn Ile Pro Leu Leu Ile Ala Gly
            130                 135                140
Val Ile Gly Gly Ser Tyr Ser Ser Val Ser Ile Gln Val Ala Asn Leu
145                 150                 155                160
Leu Arg Leu Phe Gln Ile Pro Gln Ile Ser Tyr Ala Ser Thr Ser Ala
                165                 170                175
Lys Leu Ser Asp Lys Ser Arg Tyr Asp Tyr Phe Ala Arg Thr Val Pro
            180                 185                190
Pro Asp Phe Tyr Gln Ala Lys Ala Met Ala Glu Ile Leu Arg Phe Phe
            195                 200                205
Asn Trp Thr Tyr Val Ser Thr Val Ala Ser Glu Gly Asp Tyr Gly Glu
            210                 215                220
Thr Gly Ile Glu Ala Phe Glu Gln Glu Ala Arg Leu Arg Asn Ile Cys
225                 230                 235                240
Ile Ala Thr Ala Glu Lys Val Gly Arg Ser Asn Ile Arg Lys Ser Tyr
            245                 250                255
Asp Ser Val Ile Arg Glu Leu Leu Gln Lys Pro Asn Ala Arg Val Val
            260                 265                270
Val Leu Phe Met Arg Ser Asp Asp Ser Arg Glu Leu Ile Ala Ala Ala
            275                 280                285
Ser Arg Ala Asn Ala Ser Phe Thr Trp Val Ala Ser Asp Gly Trp Gly
            290                 295                300
Ala Gln Glu Ser Ile Ile Lys Gly Ser Glu His Val Ala Tyr Gly Ala
305                 310                 315                320
Ile Thr Leu Glu Leu Ala Ser Gln Pro Val Arg Gln Phe Asp Arg Tyr
                325                 330                335
Phe Gln Ser Leu Asn Pro Tyr Asn Asn His Arg Asn Pro Trp Phe Arg
            340                 345                350
```

-continued

```
Asp Phe Trp Glu Gln Lys Phe Gln Cys Ser Leu Gln Asn Lys Arg Asn
        355                 360                 365

His Arg Arg Val Cys Asp Lys His Leu Ala Ile Asp Ser Ser Asn Tyr
        370                 375                 380

Glu Gln Glu Ser Lys Ile Met Phe Val Val Asn Ala Val Tyr Ala Met
385                 390                 395                 400

Ala His Ala Leu His Lys Met Gln Arg Thr Leu Cys Pro Asn Thr Thr
                405                 410                 415

Lys Leu Cys Asp Ala Met Lys Ile Leu Asp Gly Lys Lys Leu Tyr Lys
                420                 425                 430

Asp Tyr Leu Leu Lys Ile Asn Phe Thr Ala Pro Phe Asn Pro Asn Lys
            435                 440                 445

Asp Ala Asp Ser Ile Val Lys Phe Asp Thr Phe Gly Asp Gly Met Gly
450                 455                 460

Arg Tyr Asn Val Phe Asn Phe Gln Asn Val Gly Gly Lys Tyr Ser Tyr
465                 470                 475                 480

Leu Lys Val Gly His Trp Ala Glu Thr Leu Ser Leu Asp Val Asn Ser
                485                 490                 495

Ile His Trp Ser Arg Asn Ser Val Pro Thr Ser Gln Cys Ser Asp Pro
                500                 505                 510

Cys Ala Pro Asn Glu Met Lys Asn Met Gln Pro Gly Asp Val Cys Cys
                515                 520                 525

Trp Ile Cys Ile Pro Cys Glu Pro Tyr Glu Tyr Leu Ala Asp Glu Phe
            530                 535                 540

Thr Cys Met Asp Cys Gly Ser Gly Gln Trp Pro Thr Ala Asp Leu Thr
545                 550                 555                 560

Gly Cys Tyr Asp Leu Pro Glu Asp Tyr Ile Arg Trp Glu Asp Ala Trp
                565                 570                 575

Ala Ile Gly Pro Val Thr Ile Ala Cys Leu Gly Phe Met Cys Thr Cys
            580                 585                 590

Met Val Val Thr Val Phe Ile Lys His Asn Asn Thr Pro Leu Val Lys
                595                 600                 605

Ala Ser Gly Arg Glu Leu Cys Tyr Ile Leu Leu Phe Gly Val Gly Leu
            610                 615                 620

Ser Tyr Cys Met Thr Phe Phe Phe Ile Ala Lys Pro Ser Pro Val Ile
625                 630                 635                 640

Cys Ala Leu Arg Arg Leu Gly Leu Gly Ser Ser Phe Ala Ile Cys Tyr
                645                 650                 655

Ser Ala Leu Leu Thr Lys Thr Asn Cys Ile Ala Arg Ile Phe Asp Gly
            660                 665                 670

Val Lys Asn Gly Ala Gln Arg Pro Lys Phe Ile Ser Pro Ser Ser Gln
            675                 680                 685

Val Phe Ile Cys Leu Gly Leu Ile Leu Val Gln Ile Val Met Val Ser
            690                 695                 700

Val Trp Leu Ile Leu Glu Ala Pro Gly Thr Arg Arg Tyr Thr Leu Ala
705                 710                 715                 720

Glu Lys Arg Glu Thr Val Ile Leu Lys Cys Asn Val Lys Asp Ser Ser
                725                 730                 735

Met Leu Ile Ser Leu Thr Tyr Asp Val Ile Leu Val Ile Leu Cys Thr
                740                 745                 750

Val Tyr Ala Phe Lys Thr Arg Lys Cys Pro Glu Asn Phe Asn Glu Ala
            755                 760                 765
```

```
Lys Phe Ile Gly Phe Thr Met Tyr Thr Thr Cys Ile Ile Trp Leu Ala
    770             775             780
Phe Leu Pro Ile Phe Tyr Val Thr Ser Ser Asp Tyr Arg Val Gln Thr
785             790             795             800
Thr Thr Met Cys Ile Ser Val Ser Leu Ser Gly Phe Val Val Leu Gly
            805             810             815
Cys Leu Phe Ala Pro Lys Val His Ile Ile Leu Phe gln Pro Gln Lys
            820             825             830
Asn Val Val Thr His Arg Leu His Leu Asn Arg Phe Ser Val Ser Gly
            835             840             845
Thr Gly Thr Thr Tyr Ser Gln Ser Ser Ala Ser Thr Tyr Val Pro Thr
            850             855             860
Val Cys Asn Gly Arg Glu Val Leu Asp Ser Thr Thr Ser Ser Leu
865             870             875
                                                20
``` which is hereinafter designated as SEQ ID NO:2.

The invention further provides an isolated nucleic acid compound that comprises a nucleic acid sequence which encodes for the amino acid compounds provided. Particularly, this invention provides the isolated nucleic acid compound having the sequence:

```
ATG AAC ATG TTG ACA AGA CTG CAA GTT CTT ACC TTA GCT TTG TTT TCA  48
Met Lys Met Leu Thr Arg Leu Gln Val Leu Thr Leu Ala Leu Phe Ser
 1               5                  10                  15

AAG GGA TTT TTA CTC TCT TTA GGG GAC CAT AAC TTT CTA AGG AGA GAG  96
Lys Gly Phe Leu Leu Ser Leu Gly Asp His Asn Phe Leu Arg Arg Glu
             20                  25                  30

ATT AAA ATA GAA GGT GAC CTT GTT TTA GGG GGC CTG TTT CCT ATT AAC 144
Ile Lys Ile Glu Gly Asp Leu Val Leu Gly Gly Leu Phe Pro Ile Asn
                 35                  40                  45

GAA AAA GGC ACT GGA ACT GAA GAA TGT GGG CGA ATC AAT GAA GAC CGA 192
Glu Lys Gly Thr Gly Thr Glu Glu Cys Gly Arg Ile Asn Glu Asp Arg
         50                  55                  60

GGG ATT CAA CGC CTG GAA GCC ATG TTG TTT GCT ATT GAT GAA ATC AAC 240
Gly Ile Gln Arg Leu Glu Ala Met Leu Phe Ala Ile Asp Glu Ile Asn
 65                  70                  75                  80

AAA GAT GAT TAC TTG CTA CCA GGA GTG AAG TTG GGT GTT CAC ATT TTG 288
Lys Asp Asp Tyr Leu Leu Pro Gly Val Lys Leu Gly Val His Ile Leu
                 85                  90                  95

GAT ACA TGT TCA AGG GAT ACC TAT GCA TTG GAG CAA TCA CTG GAG TTT 336
Asp Thr Cys Ser Arg Asp Thr Tyr Ala Leu Glu Gln Ser Leu Glu Phe
            100                 105                 110

GTC AGG GCA TCT TTG ACA AAA GTG GAT GAA GCT GAG TAT ATG TGT CCT 384
Val Arg Ala Ser Leu Thr Lys Val Asp Glu Ala Glu Tyr Met Cys Pro
        115                 120                 125

GAT GGA TCC TAT GCC ATT CAA GAA AAC ATC CCA CTT CTC ATT GCA GGG 432
Asp Gly Ser Tyr Ala Ile Gln Glu Asn Ile Pro Leu Leu Ile Ala Gly
    130                 135                 140

GTC ATT GGT GGC TCT TAT AGC AGT GTT TCC ATA CAG GTG GCA AAC CTG 480
Val Ile Gly Gly Ser Tyr Ser Ser Val Ser Ile Gln Val Ala Asn Leu
145                 150                 155                 160

CTG CGG CTC TTC CAG ATC CCT CAG ATC AGC TAC GCA TCC ACC AGC GCC 528
Leu Arg Leu Phe Gln Ile Pro Gln Ile Ser Tyr Ala Ser Thr Ser Ala
                165                 170                 175

AAA CTC AGT GAT AAG TCG CGC TAT GAT TAC TTT GCC AGG ACC GTG CCC 576
Lys Leu Ser Asp Lys Ser Arg Tyr Asp Tyr Phe Ala Arg Thr Val Pro
            180                 185                 190

CCC GAC TTC TAC CAG GCC AAA GCC ATG GCT GAG ATC TTG CGC TTC TTC 624
Pro Asp Phe Tyr Gln Ala Lys Ala Met Ala Glu Ile Leu Arg Phe Phe
        195                 200                 205
```

```
AAC TGG ACC TAC GTG TCC ACA GTA GCC TCC GAG GGT GAT TAC GGG GAG    672
Asn Trp Thr Tyr Val Ser Thr Val Ala Ser Glu Gly Asp Tyr Gly Glu
    210                 215                 220

ACA GGG ATC GAG GCC TTC GAG CAG GAA GCC CGC CTG CGC AAC ATC TGC    720
Thr Gly Ile Glu Ala Phe Glu Gln Glu Ala Arg Leu Arg Asn Ile Cys
225                 230                 235                 240

ATC GCT ACG GCG GAG AAG GTG GGC CGC TCC AAC ATC CGC AAG TCC TAC    768
Ile Ala Thr Ala Glu Lys Val Gly Arg Ser Asn Ile Arg Lys Ser Tyr
                245                 250                 255

GAC AGC GTG ATC CGA GAA CTG TTG CAG AAG CCC AAC GCG CGC GTC GTG    816
Asp Ser Val Ile Arg Glu Leu Leu Gln Lys Pro Asn Ala Arg Val Val
            260                 265                 270

GTC CTC TTC ATG CGC AGC GAC GAC TCG CGG GAG CTC ATT GCA GCC GCC    864
Val Leu Phe Met Arg Ser Asp Asp Ser Arg Glu Leu Ile Ala Ala Ala
        275                 280                 285

AGC CGC GCC AAT GCC TCC TTC ACC TGG GTG GCC AGC GAC GGC TGG GGC    912
Ser Arg Ala Asn Ala Ser Phe Thr Trp Val Ala Ser Asp Gly Trp Gly
    290                 295                 300

GCG CAG GAG AGC ATC ATC AAG GGC AGC GAG CAT GTG GCC TAC GGC GCC    960
Ala Gln Glu Ser Ile Ile Lys Gly Ser Glu His Val Ala Tyr Gly Ala
305                 310                 315                 320

ATC ACC CTG GAG CTG GCC TCC CAG CCT GTC CGC CAG TTC GAC CGC TAC    1008
Ile Thr Leu Glu Leu Ala Ser Gln Pro Val Arg Gln Phe Asp Arg Tyr
                325                 330                 335

TTC CAG AGC CTC AAC CCC TAC AAC AAC CAC CGC AAC CCC TGG TTC CGG    1056
Phe Gln Ser Leu Asn Pro Tyr Asn Asn His Arg Asn Pro Trp Phe Arg
            340                 345                 350

GAC TTC TGG GAG CAA AAG TTT CAG TGC AGC CTC CAG AAC AAA CGC AAC    1104
Asp Phe Trp Glu Gln Lys Phe Gln Cys Ser Leu Gln Asn Lys Arg Asn
        355                 360                 365

CAC AGG CGC GTC TGC GAC AAG CAC CTG GCC ATC GAC AGC AGC AAC TAC    1152
His Arg Arg Val Cys Asp Lys His Leu Ala Ile Asp Ser Ser Asn Tyr
    370                 375                 380

GAG CAA GAG TCC AAG ATC ATG TTT GTG GTG AAC GCG GTG TAT GCC ATG    1200
Glu Gln Glu Ser Lys Ile Met Phe Val Val Asn Ala Val Tyr Ala Met
385                 390                 395                 400

GCC CAC GCT TTG CAC AAA ATG CAG CGC ACC CTC TGT CCC AAC ACT ACC    1248
Ala His Ala Leu His Lys Met Gln Arg Thr Leu Cys Pro Asn Thr Thr
                405                 410                 415

AAG CTT TGT GAT GCT ATG AAG ATC CTG GAT GGG AAG AAG TTG TAC AAG    1296
Lys Leu Cys Asp Ala Met Lys Ile Leu Asp Gly Lys Lys Leu Tyr Lys
            420                 425                 430

GAT TAC TTG CTG AAA ATC AAC TTC ACG GCT CCA TTC AAC CCA AAT AAA    1344
Asp Tyr Leu Leu Lys Ile Asn Phe Thr Ala Pro Phe Asn Pro Asn Lys
        435                 440                 445

GAT GCA GAT AGC ATA GTC AAG TTT GAC ACT TTT GGA GAT GGA ATG GGG    1392
Asp Ala Asp Ser Ile Val Lys Phe Asp Thr Phe Gly Asp Gly Met Gly
    450                 455                 460

CGA TAC AAC GTG TTC AAT TTC CAA AAT GTA GGT GGA AAG TAT TCC TAC    1440
Arg Tyr Asn Val Phe Asn Phe Gln Asn Val Gly Gly Lys Tyr Ser Tyr
465                 470                 475                 480

TTG AAA GTT GGT CAC TGG GCA GAA ACC TTA TCG CTA GAT GTC AAC TCT    1488
Leu Lys Val Gly His Trp Ala Glu Thr Leu Ser Leu Asp Val Asn Ser
                485                 490                 495

ATC CAC TGG TCC CGG AAC TCA GTC CCC ACT TCC CAG TGC AGC GAC CCC    1536
Ile His Trp Ser Arg Asn Ser Val Pro Thr Ser Gln Cys Ser Asp Pro
            500                 505                 510

TGT GCC CCC AAT GAA ATG AAG AAT ATG CAA CCA GGG GAT GTC TGC TGC    1584
Cys Ala Pro Asn Glu Met Lys Asn Met Gln Pro Gly Asp Val Cys Cys
        515                 520                 525
```

-continued

```
TGG ATT TGC ATC CCC TGT GAA CCC TAC GAA TAC CTG GCT GAT GAG TTT    1632
Trp Ile Cys Ile Pro Cys Glu Pro Tyr Glu Tyr Leu Ala Asp Glu Phe
    530                 535                 540

ACC TGT ATG GAT TGT GGG TCT GGA CAG TGG CCC ACT GCA GAC CTA ACT    1680
Thr Cys Met Asp Cys Gly Ser Gly Gln Trp Pro Thr Ala Asp Leu Thr
545                 550                 555                 560

GGA TGC TAT GAC CTT CCT GAG GAC TAC ATC AGG TGG GAA GAC GCC TGG    1728
Gly Cys Tyr Asp Leu Pro Glu Asp Tyr Ile Arg Trp Glu Asp Ala Trp
                565                 570                 575

GCC ATT GGC CCA GTC ACC ATT GCC TGT CTG GGT TTT ATG TGT ACA TGC    1776
Ala Ile Gly Pro Val Thr Ile Ala Cys Leu Gly Phe Met Cys Thr Cys
            580                 585                 590

ATG GTT GTA ACT GTT TTT ATC AAG CAC AAC AAC ACA CCC TTG GTC AAA    1824
Met Val Val Thr Val Phe Ile Lys His Asn Asn Thr Pro Leu Val Lys
        595                 600                 605

GCA TCG GGC CGA GAA CTC TGC TAC ATC TTA TTG TTT GGG GTT GGC CTG    1872
Ala Ser Gly Arg Glu Leu Cys Tyr Ile Leu Leu Phe Gly Val Gly Leu
    610                 615                 620

TCA TAC TGC ATG ACA TTC TTC TTC ATT GCC AAG CCA TCA CCA GTC ATC    1920
Ser Tyr Cys Met Thr Phe Phe Phe Ile Ala Lys Pro Ser Pro Val Ile
625                 630                 635                 640

TGT GCA TTG CGC CGA CTC GGG CTG GGG AGT TCC TTC GCT ATC TGT TAC    1968
Cys Ala Leu Arg Arg Leu Gly Leu Gly Ser Ser Phe Ala Ile Cys Tyr
                645                 650                 655

TCA GCC CTG CTG ACC AAG ACA AAC TGC ATT GCC CGC ATC TTC GAT GGG    2016
Ser Ala Leu Leu Thr Lys Thr Asn Cys Ile Ala Arg Ile Phe Asp Gly
            660                 665                 670

GTC AAG AAT GGC GCT CAG AGG CCA AAA TTC ATC AGC CCC AGT TCT CAG    2064
Val Lys Asn Gly Ala Gln Arg Pro Lys Phe Ile Ser Pro Ser Ser Gln
        675                 680                 685

GTT TTC ATC TGC CTG GGT CTG ATC CTG GTG CAA ATT GTG ATG GTG TCT    2112
Val Phe Ile Cys Leu Gly Leu Ile Leu Val Gln Ile Val Met Val Ser
    690                 695                 700

GTG TGG CTC ATC CTG GAG GCC CCA GGC ACC AGG AGG TAT ACC CTT GCA    2160
Val Trp Leu Ile Leu Glu Ala Pro Gly Thr Arg Arg Tyr Thr Leu Ala
705                 710                 715                 720

GAG AAG CGG GAA ACA GTC ATC CTA AAA TGC AAT GTC AAA GAT TCC AGC    2208
Glu Lys Arg Glu Thr Val Ile Leu Lys Cys Asn Val Lys Asp Ser Ser
                725                 730                 735

ATG TTG ATC TCT CTT ACC TAC GAT GTG ATC CTG GTG ATC TTA TGC ACT    2256
Met Leu Ile Ser Leu Thr Tyr Asp Val Ile Leu Val Ile Leu Cys Thr
            740                 745                 750

GTG TAC GCC TTC AAA ACG CGG AAG TGC CCA GAA AAT TTC AAC GAA GCT    2304
Val Tyr Ala Phe Lys Thr Arg Lys Cys Pro Glu Asn Phe Asn Glu Ala
        755                 760                 765

AAG TTC ATA GGT TTT ACC ATG TAC ACC ACG TGC ATC ATC TGG TTG GCC    2352
Lys Phe Ile Gly Phe Thr Met Tyr Thr Thr Cys Ile Ile Trp Leu Ala
    770                 775                 780

TTC CTC CCT ATA TTT TAT GTG ACA TCA AGT GAC TAC AGA GTG CAG ACG    2400
Phe Leu Pro Ile Phe Tyr Val Thr Ser Ser Asp Tyr Arg Val Gln Thr
785                 790                 795                 800

ACA ACC ATG TGC ATC TCT GTC AGC CTG AGT GGC TTT GTG GTC TTG GGC    2448
Thr Thr Met Cys Ile Ser Val Ser Leu Ser Gly Phe Val Val Leu Gly
                805                 810                 815

TGT TTG TTT GCA CCC AAG GTT CAC ATC ATC CTG TTT CAA CCC CAG AAG    2496
Cys Leu Phe Ala Pro Lys Val His Ile Ile Leu Phe Gln Pro Gln Lys
            820                 825                 830

AAT GTT GTC ACA CAC AGA CTG CAC CTC AAC AGG TTC AGT GTC AGT GGA    2544
Asn Val Val Thr His Arg Leu His Leu Asn Arg Phe Ser Val Ser Gly
        835                 840                 845
```

-continued

```
ACT GGG ACC ACA TAC TCT CAG TCC TCT GCA AGC ACG TAT GTG CCA ACG   2592
Thr Gly Thr Thr Tyr Ser Gln Ser Ser Ala Ser Thr Tyr Val Pro Thr
    850                     855                 860

GTG TGC AAT GGG CGG GAA GTC CTC GAC TCC ACC ACC TCA TCT CTG       2637
Val Cys Asn Gly Arg Glu Val Leu Asp Ser Thr Thr Ser Ser Leu
865                 870                 875
``` which is hereinafter designated as SEQ ID NO:1.

The present invention provides the protein of SEQ ID NO:2, a human metabotropic glutamate receptor, designated as a HmGluR3 receptor using the nomenclature system described in D. D. Schoepp, "Glutamate receptors", Handbook of Receptors and Channels, Chapter 13 (S. J. Peroutka, ed., CRC Press, 1984). Based on the rat cognate of this receptor, the mGluR3 receptor is believed to be found throughout many regions of the brain. Expression of the receptor has been found in neuronal cells of the cerebral cortex, thalamic reticular nucleus, supraoptic nucleus and the granule cells in the dentate gyrus. Expression of the mGluR3 receptor has also been found in glial cells in white matter such as the corpus callosum and anterior commissure. Moderate expression has also been seen in Golgi cells. See Tanabe et al, *J. Neurosci.*, 13(4), 1372–78 (1993). This receptor is believed to potentiate central nervous system responses and is, therefore, an important target for pharmaceutical purposes.

Skilled artisans will recognize that the proteins of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See. e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl

Asp, cyclohexyl

Glu, cyclohexyl

Ser, Benzyl

Thr, Benzyl

Tyr, 4-bromo carbobenzoxy

Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% metacresol. Cleavage of the side chain protecting group(s) and of the peptide from the resin is carried out at zero degrees Celcius or below, preferably $-20°$ C. for thirty minutes followed by thirty minutes at $0°$ C.

After removal of the hydrogen fluoride, the peptide/resin is washed with ether, and the peptide extracted with glacial acetic acid and then lyophilized. Purification is accomplished by size-exclusion chromatography on a Sephadex G-10 (Pharmacia) column in 10% acetic acid.

The proteins of the present invention can also be produced by recombinant methods. Recombinant methods are preferred if a high yield is desired. A general method for the construction of any desired DNA sequence is provided in J. Brown, et al., *Methods in Enzymology*, 68:109 (1979). See also, J. Sambrook, et al., supra.

The basic steps in the recombinant production of desired proteins are:

a) construction of a natural, synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences and constructing the vectors of the present invention. Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following:

| Strain | Genotype |
| --- | --- |
| DH5α | F− (φ80dlacZΔM15), Δ(lacZYA-argF)U169 supE44, λ−· hsdR17($r_K^-$, $m_K^+$), recA1, endA1, gyrA96, thi-1, relA1 |
| HB101 | supE44, hsdS20($r_B^-$ $m_B^-$), recA13, ara-14, proA2 lacY1, galK2, rpsL20, xyl-5, mtl-1, mcrB, mrr |
| JM109 | recA1, e14−(mcrA), supE44, endA1, hsdR17($r_K^-$, $m_K^+$), gyrA96, relA1, thi-1, Δ(lac-proAB), F′[traD36, proAB+ lacI$^q$,lacZΔM15] |
| RR1 | supE44, hsdS20($r_B^-$ $m_B^-$), ara-14 proA2, lacY1, galK2, rpsL20, xyl-5, mtl-5 |
| χ1776 | F−, ton, A53, dapD8, minA1, supE42 (glnV42), Δ(gal-uvrB)40, minB2, rfb-2, gyrA25, thyA142, oms-2, metC65, oms-1, Δ(bioH-asd)29, cycB2, cycA1, hsdR2, λ− |

-continued

| Strain | Genotype |
| --- | --- |
| 294 | endA, thi⁻, hsr⁻, hsm_k⁺ (U.S. Pat. No. 4,366,246) |
| XL1 Blue | recA1, endA1, gyrA96, thi, hsdR17(r_k,m_k+), supE44, relA1, λ⁻, Δ(lac), [F', proAB, laclqZΔM15, Tn10(tet$^R$)] |

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra.

In addition to the strains of E. coli discussed supra, bacilli such as Bacillus subtilis, other enterobacteriaceae such as Salmonella typhimurium or Serratia marcescans, and various Pseudomonas species may be used. In addition to these gram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., Nature (London), 275:615 (1978); and Goeddel et al., Nature (London), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in Protein Purification: From Molecular Mechanisms to Large Scale Processes, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the human glutamate receptor-encoding nucleic acids of the present invention. Exemplary host cells suitable for use in the present invention are listed below in TABLE I

TABLE I

| Host Cell | Origin | Source |
| --- | --- | --- |
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7.1 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| HS-Sultan | Human Plasma Cell Plasmocytoma | ATCC CCL 1484 |
| BHK-21 | Baby Hamster Kidney | ATCC CCL 10 |

A preferred cell line employed in this invention is the widely available cell line AV12-664 (hereinafter referred to as "AV12"). This cell line is available from the American Type Culture Collection under the accession number ATCC CRL 9595. The AV12 cell line was derived by injecting a Syrian hamster in the scruff of the neck with human adenovirus 12 and then isolating and culturing cells from the resulting tumor.

Cell lines, such as AV12, produce glutamate endogenously. As a result, substantial amounts of glutamate are secreted into the culture medium thereby making it somewhat difficult to express and study glutamate receptors in such cell lines due to the activation of the transfected receptor. Mechanisms such as the use of an effective glutamate transport system can be employed to remove excess glutmate effectively.

Therefore, a more preferred cell line for use in the present invention is the cell line RGT-18 (hereinafter referred to as "RGT"). The RGT cell line is constructed by transfecting the cell line AV12 with an expression plasmid in which the rat glutamate transporter gene (GLAST) is expressed. The glutamate level in 24 hour medium of RGT is reduced to less than 3 micromolar, thus reducing the basal activation of the receptor and/or desensitation or the requirement for extensive washing to remove residual glutamate before assay procedures. See Storck, et al, Proc. Nat'l Acad. Sci. USA, 89:10955–59 (Nov. 1992) and Desai et al, Molecular Pharmacology, 48:648–657 (1995).

A wide variety of vectors, some of which are discussed below, exist for the transformation of mammalian host cells such as those described above. The specific vectors described herein are in no way intended to limit the scope of the present invention. The expression vectors of the present invention were constructed so that DNA molecules encoding useful substances can be or have been readily inserted into the vectors in the correct position for expression.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., J. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA)*, 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

A preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A(E1A) gene product. The E1A gene product (actually, the E1A gene produces two products, which are collectively referred to herein as "the E1A gene product") is an immediate-early gene product of adenovirus, a large DNA virus.

An especially preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. Nos. 5,242,688, issued Sep. 7, 1993, and 4,992,373, issued Feb. 12, 1991, as well as co-pending U.S. patent application Ser. No. 08/208,930 and EPO Publication Number 245 949, published on Nov. 19, 1987, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

An even more preferred expression vector within the phd series is the plasmid pGTh. The pGTh plasmid contains a unique BclI site which allows for the insertion of a gene encoding the protein of interest and also contains a gene encoding the hygromycin resistance determinant. The skilled artisan understands that linkers or adapters may be employed in cloning the gene of interest into this BclI site. Plasmid pGTh contains the following elements beginning at the EcoR1 site and proceeding counterclockwise: the EcoR1 to blunt-ended NdeI fragment of pBR322 containing the ampicillin resistant gene and origin of replicaiton; the PvuII to blunt-ended BamHI fragment of pSV2-hyg' [derivative of pSV2-hyg constructed by A. Smith and P. Berg] containing a hygromycin phosphotransferase (HYPR) expression cistron; the blunt-ended NdeI(nt 2297) to AccI (nt 2246) restriction fragment of pBR322; the ACCI (nt 4339) to StuI (nt 5122) restriction fragment of BKV-P2; the GBMT HindIII promoter cassette; HindIII and BclI linker; the 610bp MhoI fragment of simian virus 40 (SV40) containing a splice junction; the 988 bp BclI to EcoRI fragment of SV40 containing the polyadenylation signal. See Berg et al, *Biotechniques*, 14:972–978 (1993).

The pGTh series of plasmids functions most efficiently when introduced into a host cell which produces the E1A gene product, cell lines such as AV12-664 (AV12), RGT-18 (RGT), 293 cells, and others, described supra. The construction and method of using the pGTh plasmid is described in detail in Berg et al., supra, European Patent Application Publication 0445939 published on Sep. 11, 1991 and U.S. patent application Ser. No. 08/446,126, filed May 19, 1995, incorporated herein by reference. Plasmid pGTh can be isolated from *E. coli* K12 AG1/pGTh, which is deposited with the Northern Regional Research Laboratory under accession number NRRL B-18592.

Transfection of mammalian cells with the vectors can be performed by any of the known processes including, but not limited to, the protoplast fusion method, the calcium phosphate co-precipitation method, electroporation and the like. See. e.g., J. Sambrook, et al., supra, at 3:16.30–3:16.66.

Other routes of production are well known to skilled artisans. In addition to the plasmids discussed above, it is well known in the art that some viruses are also appropriate vectors. For example, the adenoviruses, the adeno-associated viruses, the vaccinia virus, the herpes viruses, the baculoviruses, and the rous sarcoma virus are useful. Such a method is described in U.S. Pat. No. 4,775,624, incorporated herein by reference. Several alternate methods of expression are described in J. Sambrook, et al., supra, at 16.3–17.44.

In addition to prokaryotes and mammalian host cells, eukaryotic microbes such as yeast cultures may also be used.

The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See. e.g., L. Stinchcomb, et al., *Nature*, 282:39 (1979); J. Kingsman et al., *Gene*, 7:141 (1979); S. Tschemper et al., *Gene*, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, incorporated herein by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, incorporated herein by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, incorporated herein by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conduction with the CYC1 promoter on plasmid YEpsec—hI1beta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typically such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which may be functional equivalents of the protein of SEQ ID NO:2 are shown in TABLE II, infra.

TABLE II

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Met | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encode these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human glutamate HmGluR3 receptor molecule may be produced using synthetic methodology. This synthesis of nucleic acids is well known in the art. See. e.g., E. L. Brown, R. Belagaje, M. J. Ryan, and H. G. Khorana, *Methods in Enzymology*, 68:109–151 (1979). The DNA segments corresponding to the receptor gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. [(See. e.g., M. J. Gait, ed., *Oligonucleotide Synthesis, A Practical Approach*, (1984).]

The synthetic human glutamate HmGluR3 receptor gene may be designed to possess restriction endonuclease cleavage sites at either end of the transcript to facilitate isolation from and integration into expression and amplification plasmids. The choice of restriction sites are chosen so as to properly orient the coding sequence of the receptor with control sequences to achieve proper in-frame reading and expression of the HmGluR3 receptor molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is incorporated herein by reference.

In addition to the deoxyribonucleic acid of SEQ ID NO:1, this invention also provides ribonucleic acids (RNA) which comprise the RNA sequence:

synthetic methods discussed supra or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1 or SEQ ID NO:3.

| | | | | | |
|---|---|---|---|---|---|
| AUGAAGAUGU | UGACAAGACU | GCAAGUUCUU | ACCUUAGCUU | UGUUUUCAAA | 50 |
| GGGAUUUUUA | CUCUCUUUAG | GGGACCAUAA | CUUUCUAAGG | AGAGAGAUUA | 100 |
| AAAUAGAAGG | UGACCUUGUU | UUAGGGGGCC | UGUUUCCUAU | UAACGAAAAA | 150 |
| GGCACUGGAA | CUGAAGAAUG | UGGGCGAAUC | AAUGAAGACC | GAGGGAUUCA | 200 |
| ACGCCUGGAA | GCCAUGUUGU | UUGCUAUUGA | UGAAAUCAAC | AAAGAUGAUU | 250 |
| ACUUGCUACC | AGGAGUGAAG | UUGGGUGUUC | ACAUUUUGGA | UACAUGUUCA | 300 |
| AGGGAUACCU | AUGCAUUGGA | GCAAUCACUG | GAGUUUGUCA | GGGCAUCUUU | 350 |
| GACAAAAGUG | GAUGAAGCUG | AGUAUAUGUG | UCCUGAUGGA | UCCUAUGCCA | 400 |
| UUCAAGAAAA | CAUCCCACUU | CUCAUUGCAG | GGGUCAUUGG | UGGCUCUUAU | 450 |
| AGCAGUGUUU | CCAUACAGGU | GGCAAACCUG | CUGCGGCUCU | UCCAGAUCCC | 500 |
| UCAGAUCAGC | UACGCAUCCA | CCAGCGCCAA | ACUCAGUGAU | AAGUCGCGCU | 550 |
| AUGAUUACUU | UGCCAGGACC | GUGCCCCCCG | ACUUCUACCA | GGCCAAAGCC | 600 |
| AUGGCUGAGA | UCUUGCGCUU | CUUCAACUGG | ACCUACGUGU | CCACAGUAGC | 650 |
| CUCCGAGGGU | GAUUACGGGG | AGACAGGGAU | CGAGGCCUUC | GAGCAGGAAG | 700 |
| CCCGCCUGCG | CAACAUCUGC | AUCGCUACGG | CGGAGAAGGU | GGGCCGCUCC | 750 |
| AACAUCCGCA | AGUCCUACGA | CAGCGUGAUC | CGAGAACUGU | UGCAGAAGCC | 800 |
| CAACGCGCGC | GUCGUGGUCC | UCUUCAUGCG | CAGCGACGAC | UCGCGGGAGC | 850 |
| UCAUUGCAGC | CGCCAGCCGC | GCCAAUGCCU | CCUUCACCUG | GGUGGCCAGC | 900 |
| GACGGCUGGG | GCGCGCAGGA | GAGCAUCAUC | AAGGGCAGCG | AGCAUGUGGC | 950 |
| CUACGGCGCC | AUCACCCUGG | AGCUGGCCUC | CCAGCCUGUC | CGCCAGUUCG | 1000 |
| ACCGCUACUU | CCAGAGCCUC | AACCCCUACA | ACAACCACCG | CAACCCCUGG | 1050 |
| UUCCGGGACU | UCUGGGAGCA | AAAGUUUCAG | UGCAGCCUCC | AGAACAAACG | 1100 |
| CAACCACAGG | CGCGUCUGCG | ACAAGCACCU | GGCCAUCGAC | AGCAGCAACU | 1150 |
| ACGAGCAAGA | GUCCAAGAUC | AUGUUUGUGG | UGAACGCGGU | GUAUGCCAUG | 1200 |
| GCCCACGCUU | UGCACAAAAU | GCAGCGCACC | CUCUGUCCCA | ACACUACCAA | 1250 |
| GCUUUGUGAU | GCUAUGAAGA | UCCUGGAUGG | GAAGAAGUUG | UACAAGGAUU | 1300 |
| ACUUGCUGAA | AAUCAACUUC | ACGGCUCCAU | UCAACCCAAA | UAAAGAUGCA | 1350 |
| GAUAGCAUAG | UCAAGUUUGA | CACUUUUGGA | GAUGGAAUGG | GGCGAUACAA | 1400 |
| CGUGUUCAAU | UUCCAAAAUG | UAGGUGGAAA | GUAUUCCUAC | UUGAAAGUUG | 1450 |
| GUCACUGGGC | AGAAACCUUA | UCGCUAGAUG | UCAACUCUAU | CCACUGGUCC | 1500 |
| CGGAACUCAG | UCCCCACUUC | CCAGUGCAGC | GACCCCUGUG | CCCCCAAUGA | 1550 |
| AAUGAAGAAU | AUGCAACCAG | GGGAUGUCUG | CUGCUGGAUU | UGCAUCCCCU | 1600 |
| GUGAACCCUA | CGAAUACCUG | GCUGAUGAGU | UUACCUGUAU | GGAUUGUGGG | 1650 |
| UCUGGACAGU | GGCCCACUGC | AGACCUAACU | GGAUGCUAUG | ACCUUCCUGA | 1700 |
| GGACUACAUC | AGGUGGGAAG | ACGCCUGGGC | CAUUGGCCCA | GUCACCAUUG | 1750 |
| CCUGUCUGGG | UUUUAUGUGU | ACAUGCAUGG | UUGUAACUGU | UUUUAUCAAG | 1800 |
| CACAACAACA | CACCCUUGGU | CAAAGCAUCG | GGCCGAGAAC | UCUGCUACAU | 1850 |
| CUUAUUGUUU | GGGGUUGGCC | UGUCAUACUG | CAUGACAUUC | UUCUUCAUUG | 1900 |
| CCAAGCCAUC | ACCAGUCAUC | UGUGCAUUGC | GCCGACUCGG | GCUGGGGAGU | 1950 |
| UCCUUCGCUA | UCUGUUACUC | AGCCCUGCUG | ACCAAGACAA | ACUGCAUUGC | 2000 |
| CCGCAUCUUC | GAUGGGGUCA | AGAAUGGCGC | UCAGAGGCCA | AAAUUCAUCA | 2050 |
| GCCCCAGUUC | UCAGGUUUUC | AUCUGCCUGG | GUCUGAUCCU | GGUGCAAAUU | 2100 |
| GUGAUGGUGU | CUGUGUGGCU | CAUCCUGGAG | GCCCCAGGCA | CCAGGAGGUA | 2150 |
| UACCCUUGCA | GAGAAGCGGG | AAACAGUCAU | CCUAAAAUGC | AAUGUCAAAG | 2200 |
| AUUCCAGCAU | GUUGAUCUCU | CUUACCUACG | AUGUGAUCCU | GGUGAUCUUA | 2250 |
| UGCACUGUGU | ACGCCUUCAA | AACGCGGAAG | UGCCCAGAAA | AUUUCAACGA | 2300 |
| AGCUAAGUUC | AUAGGUUUUA | CCAUGUACAC | CACGUGCAUC | AUCUGGUUGG | 2350 |
| CCUUCCUCCC | UAUAUUUUAU | GUGACAUCAA | GUGACUACAG | AGUGCAGACG | 2400 |
| ACAACCAUGU | GCAUCUCUGU | CAGCCUGAGU | GGCUUUGUGG | UCUUGGCCUG | 2450 |
| UUUGUUUGCA | CCCAAGGUUC | ACAUCAUCCU | GUUUCAACCC | CAGAAGAAUG | 2500 |
| UUGUCACACA | CAGACUGCAC | CUCAACAGGU | UCAGUGUCAG | UGGAACUGGG | 2550 |
| ACCACAUACU | CUCAGUCCUC | UGCAAGCACG | UAUGUGCCAA | CGGUGUGCAA | 2600 |
| UGGGCGGGAA | GUCCUCGACU | CCACCACCUC | AUCUCUGUGA | | 2650 | hereinafter designated as SEQ ID NO:3, or the complementary ribonucleic acid, or a fragment of either SEQ ID NO:3 or the complement thereof. The ribonucleic acids of the present invention may be prepared using the polynucleotide The present invention also provides probes and primers useful for molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to human genomic DNA or messenger RNA encoding a human glutamate receptor, is provided. Preferably, the 18 or more base pair compound is DNA.

The term "selectively hybridize" as used herein may refer to either of two situations. In the first such embodiment of this invention, the nucleic acid compounds described supra hybridize to a human glutamate receptor under more stringent hybridization conditions than these same nucleic acid compounds would hybridize to an analogous glutamate receptor of another species, e.g. rodent. In the second such embodiment of this invention, these probes hybridize to the HmGluR3 receptor under more stringent hybridization conditions than other related compounds, including nucleic acid sequences encoding other glutamate receptors.

These probes and primers can be prepared enzymatically as described supra. In a most preferred embodiment these probes and primers are synthesized using chemical means as described supra. Probes and primers of defined structure may also be purchased commercially.

Another aspect of the present invention is recombinant DNA cloning vectors and expression vectors comprising the nucleic acids of the present invention. Many of the vectors encompassed within this invention are described above. The preferred nucleic acid vectors are those which are DNA. The most preferred recombinant DNA vector comprises the isolated DNA sequence SEQ ID NO:1. Plasmid pGTh-HmGluR3, is an especially preferred DNA vector of the present invention.

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein. The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

The plasmid pGTh-HmGluR3 can be readily modified to construct expression vectors that produce HmGluR3 receptors in a variety of organisms, including, for example, *E. coli*, Sf9 (as host for baculovirus), Spodoptera and Saccharomyces.

One of the most widely employed techniques for altering a nucleic acid sequence is by way of oligonucleotide-directed site-specific mutagenesis. B. Comack, "Current Protocols in Molecular Biology", 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for *E. coli* can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and *E. coli* cells which have been transfected and/or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is AV12. The preferred vector for expression is one which comprises SEQ ID NO:1. Another preferred host cell for this method is *E. coli*. An especially preferred expression vector in *E. coli* is one which comprises SEQ ID NO:1. Transformed host cells may be cultured under conditions well known to skilled artisans such that SEQ ID NO:2 is expressed, thereby producing HmGluR3 in the recombinant host cell.

The ability of glutamate to bind to the HmGluR3 receptor is essential in the development of a multitude of indications. In developing agents which act as antagonists or agonists of the HmGluR3 receptor, it would be desirable, therefore, to determine those agents which bind the HmGluR3 receptor. Generally, such an assay includes a method for determining whether a substance is a functional ligand of the HmGluR3 receptor, said method comprising contacting a functional compound of the HmGluR3 receptor with said substance, monitoring binding activity by physically detectable means, and identifying those substances which effect a chosen response. Preferably, the physically detectable means is competition with labeled glutamate or binding of ligand in an oocyte transient expression system The instant invention provides such a screening system useful for discovering agents which compete with glutamate for binding to the HmGluR3 receptor, said screening system comprising the steps of:

a) preparing a human HmGluR3 receptor;

b) exposing said human HmGluR3 receptor to a potential inhibitor or surrogate of the glutamate/HmGluR3 receptor complex;

c) introducing glutamate;

d) removing non-specifically bound molecules; and e) quantifying the concentration of bound potential inhibitor and/or glutamate.

This allows one to rapidly screen for inhibitors or surrogates of the formation of the glutamate/HmGluR3 receptor complex. Utilization of the screening system described above provides a sensitive and rapid means to determine compounds which interfere with the formation of the glutamate/HmGluR3 receptor complex. This screening system may also be adapted to automated procedures such as a PANDEX® (Baxter-Dade Diagnostics) system allowing for efficient high-volume screening of potential therapeutic agents.

In such a screening protocol a HmGluR3 receptor is prepared as elsewhere described herein, preferably using recombinant DNA technology. A sample of a test compound is then introduced to the reaction vessel containing the HmGluR3 receptor followed by the addition of glutamate. In the alternative the glutamate may be added simultaneously with the test compound. Unbound molecules are washed free and the eluent inspected for the presence of glutamate or the test compound.

For example, in a preferred method of the invention, radioactively or chemically labeled glutamate may be used. The eluent is then scored for the chemical label or radioactivity. The absence or diminution of the chemical label or radioactivity indicates the formation of the glutamate/HmGluR3 receptor complex. This indicates that the test compound has not effectively competed with glutamate in the formation of the glutamate/HmGluR3 receptor complex. The presence of the chemical label or radioactivity indicates that the test compound has competed with glutamate in the formation of the glutamate/HmGluR3 receptor complex. Similarly, a radioactively or chemically labeled test compound may be used in which case the same steps as outlined above would be used except that the interpretation of results would be the converse of using radioactively or chemically labelled glutamate.

As would be understood by the skilled artisan, these assays may also be performed such that the practitioner measures the radioactivity or chemical label remaining with the protein, not in the eluent. A preferred such assay employs radiolabeled glutamate. After the competition reaction has been performed the reaction mixture is then passed through a filter, the filter retaining the receptor and whatever is complexed with the receptor. The radioactivity on each filter is then measured in a scintillation counter. In such an assay higher amounts of radiolabel present indicate lower affinity for the receptor by the test compound.

The HmGluR3 receptor may be free in solution or bound to a membrane. Whether the HmGluR3 receptor is bound to a membrane or is free in solution, it is generally important that the conformation of the protein be conserved. In a preferred practice of the invention, therefore, the HmGluR3 receptor is suspended in a hydrophobic environment employing natural or synthetic detergents, membrane suspensions, and the like. Preferred detergent complexes include the zwitterionic detergent 3-[(3-cholamidopropyl)-dimethylammonio]-1-propane sulfonate ("CHAPS") as well as sodium deoxycholate.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom indicate high affinity or low affinity to HmGluR3 receptor, because skilled artisans will recognize that any information regarding binding or selectivity of a particular compound is beneficial in the pharmaceutical development of drugs.

In one such competition assay, a battery of known glutamate receptor antagonists, agonists, and partial agonists are evaluated for their relative abilities to inhibit the binding of [$^3$H]glutamate to the human HmGluR3 receptor of the present invention.

In this assay cells stably expressing the cloned human HmGluR3 receptor are harvested by centrifugation at 2200×g for 15 minutes at 4° C. Membranes for the binding assays are prepared by vortexing the cell pellet in 50 mM Tris·HCl, pH 7.4 (0.5×10$^9$ cells/30 ml). The tissue suspension is then centrifuged at 39,800×g for 10 minutes at 4° C. This procedure is repeated for a total of three washes, with a 10 minute incubation at 37° C. between the second and third washes. The final pellet is homogenized in 67 mM Tris·HCl, pH 7.4, at 12.5×10$^6$ cells/ml using a TISSUM-IZER® (Tekmar, Cincinati, Ohio) at setting 65 for 15 seconds.

Binding assays are performed in triplicate in 0.8 ml total volume. Volumes of 200 μl of membrane suspension (0.07–0.10 mg of protein) and 200 μl of drug dilution in water are added to 400 μl of 67 mM of Tris·HCl, pH 7.4, containing [$^3$H]glutamate (35 nM final concentration, 23.7 Ci/mole), calcium chloride (3 mM), pargyline (10 μM), and L-ascorbic acid (5.7 nM). The reaction mixtures are incubated at 37° C. for 15 minutes and then rapidly filtered, using a BRANDEL™ cell harvester (Model MB-48R; Brandel, Gaithersburg, Md.) over Whatman GF/B filters that had been presoaked in 0.5% polyethyleneimine and precooled with ice-cold 50 mM Tris·HCl, pH 7.4. The filters are then washed rapidly times with ice-cold (4×1 ml each).

The amount of [$^3$H]glutamate trapped on the filters is determined by liquid scintillation counting. For the competition experiments, six concentrations of displacing drugs are used, ranging from 10$^{-5}$ to 10$^{-10}$ M. The IC$_{50}$ values are determined by nonlinear regression analysis (SYSTAT™; Systat Inc., Evanston, Ill.) which may be converted to $K_i$ values using the Cheng-Prusoff equation. Y. Cheng and W. H. Prusoff, *Biochemical Pharmacology*, 22:3099–3108 (1973).

In this particular type of competition assay the following compounds are frequently used.

(a) Quisqualate—a compound of the formula

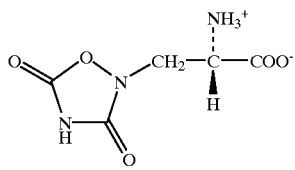

having the chemical name (S)-α-amino-3,5-dioxo-1,2,4-oxadiazolidine-2-propanoate. This compound can be prepared as described in J. E. Baldwin, et al., Chemical Communications, 256 (1985).

(b) Glutamate—a compound of the formula

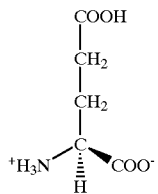

having the chemical name 1-aminopropane-1,3-dicarboxylic acid. This compound is readily available and can be purchased commercially from several sources.

(c) Ibotenate—a compound of the formula

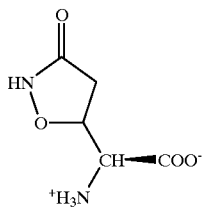

having the chemical name α-amino-3-hydroxy-5-isoxazoleacetate, which can be prepared as described in U.S. Pat. No. 3,459,862, incorporated herein by reference.

(d) t-ACPD—a compound of the formula

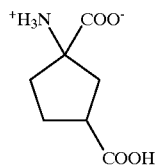

having the chemical name 1-aminocyclopentane-1,3-dicarboxylic acid. This compound can be purchased commercially from several sources.

(e) (2R,4R) 4-amino-pyrrolidine-2,4-dicarboxylic acid, a compound of the formula

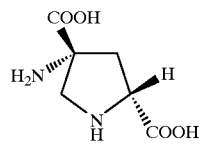

which is described in U.S. Pat. No. 5,473,077. Many 1-substituted derivatives of this dicarboxylic acid are also effective as HmGluR3 antagonists.

The previously described screening system identifies compounds which competitively bind to the HmGluR3 receptor. Determination of the ability of such compounds to stimulate or inhibit the action of the HmGluR3 receptor is essential to further development of such compounds for therapeutic applications. The need for a bioactivity assay system which determines the response of the HmGluR3 receptor to a compound is clear. The instant invention provides such a bioactivity assay, said assay comprising the steps of:

a) transfecting a mammalian host cell with an expression vector comprising DNA encoding a HmGluR3 receptor;

b) culturing said host cell under conditions such that the HmGluR3 receptor protein is expressed, c) exposing said host cell so transfected to a test compound, and d) measuring the change in a physiological condition known to be influenced by the binding of glutamate to the HmGluR3 receptor relative to a control in which the transfected host cell is exposed to glutamate.

An oocyte transient expression system can be constructed according to the procedure described in S. Lübbert, et al, Proceedings of the National Academy of Sciences (USA), 84:4332 (1987).

In an especially preferred embodiment of this invention an assay measuring the inhibition of forskolin-stimulated cAMP synthesis was performed. The inhibition of cAMP synthesis is known to positively correlated with the addition of glutamate to cells containing certain types of metabotropic receptors.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, e.g., J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See, e.g., J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is incorporated herein by reference.

The proteins of this invention as well as fragments of these proteins may be used as antigens for the synthesis of antibodies. The term "antibody" as used herein describes antibodies, fragments of antibodies (such as, but not limited, to Fab, Fab', $Fab_2$', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See. e.g., C. Milstein, *Handbook of Experimental Immunology*, (Blackwell Scientific Pub., 1986); J. Goding, *Monoclonal Antibodies: Principles and Practice*, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, et al. This reference discloses methods and vectors for the preparation of chimeric antibodies. The entire contents of U.S. Pat. No. 4,816,567 are incorporated herein by reference. An alternative approach to production of genetically engineered antibodies is provided in U.S. Pat. No. 4,816,397, which also issued Mar. 28, 1989 to M. Boss, et al., the entire contents of which are incorporated herein by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRS) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See. e.g. R. E. Bird, et al., *Science* 242:423–426 (1988); PCT Publication No. WO 88/01649, which was published Mar. 10, 1988. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of HmGluR3 receptors.

In addition to being functional as direct therapeutic and diagnostic aids, the availability of a family of antibodies which are specific for the HmGluR3 receptor enables the development of numerous assay systems for detecting agents which bind to this receptor. One such assay system comprises radiolabeling HmGluR3 receptor-specific antibodies with a radionuclide such as $^{125}I$ and measuring displacement of the radiolabeled HmGluR3 receptor-specific antibody from solid phase HmGluR3 receptor in the presence of a potential antagonist.

Numerous other assay systems are also readily adaptable to detect agents which bind HmGluR3 receptor. Examples of these aforementioned assay systems are discussed in *Methods in Enzymology*, (J. Langone. and H. Vunakis, eds. 1981), Vol. 73, Part B, the contents of which are incorporated herein by reference. Skilled artisans are directed to Section II of *Methods in Enzymology*, Vol. 73, Part B, supra, which discusses labeling of antibodies and antigens, and Section IV, which discusses immunoassay methods.

In addition to the aforementioned antibodies specific for the HmGluR3 receptor, this invention also provides antibodies which are specific for the hypervariable regions of the anti-HmGluR3 receptor antibodies. Some such anti-idiotypic antibodies would resemble the original epitope, the HmGluR3 receptor, and, therefore, would be useful in evaluating the effectiveness of compounds which are potential antagonists, agonists, or partial agonists of the HmGluR3 receptor. See. e.g., Cleveland, et al., *Nature (London)*, 305:56 (1983); Wasserman, et al., *Proceedings of the National Academy of Sciences (USA)*, 79:4810 (1982).

In another embodiment, this invention encompasses pharmaceutical formulations for parenteral administration which contain, as the active ingredient, the anti-HmGluR3 receptor antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

The following example more fully describes the present invention. Those skilled in the art will recognize that the particular reagents, equipment, and procedures described in the Example is merely illustrative and is not intended to limit the present invention in any manner.

EXAMPLES

Preparation of the RGT Cell Line

To construct the RGT cell line of the present invention, cDNA encoding the sodium dependent glutamate/asparate transporter (GLAST) was isolated from lambda ZAP® II cDNA library derived from rat hippocampus (commercially available from Stratagene, Inc., La Jolla, Calif. 92037, Catalog #936518). The GLAST published sequence (see Desai et al, supra) was used to design PCR primers which generated a 602 base pair fragment from an aliquot of the library as template. This fragment was used as a template to generate a radioactively labelled probe for screening the cDNA library. Using standard plaque hybridization techniques (moderate stringency, 1 M Na+, 60° C.), a number of positive clones were isolated. By further dilution and hybridization, a phage clone was purified which contained the complete coding sequence for the gene. The plasmid containing the insert was excised from the phage using helper phage and protocols supplied by Stratagene, Inc. The GLAST cDNA from this lambda ZAPII phage was excised on a pBluescript® phagemid vector (pBluescript® SK+).

The GLAST cDNA was removed from the phagemid on a 2.6 kb EcoRV-SmaI restriction fragment and XbaI linkers were added to each end. This fragment was introduced into the XbaI site of the mammalian expression vector pRS/RSV (commercially available from Invitrogen, Catalog #V780-20) to produce pRS151. The plasmid pRS151 was then transfected into the AV12 cell line using the calcium phosphate precipitation method (Graham et al, Virology 52:456–467, (1973)) with reagents obtained from Stragagene, Inc. Ten micrograms of plasmid were used without carrier DNA for each 10 cm petri plate of cells at approximately 50% confluancy. Clones expressing GLAST were selected by resistance to G418 (500 µg/ml, GIBCO-BRL). Clone RGT was found to accumulate less than 3 micromolar glutamate in culture when compared with parent AV12 at 100 micromolar after 24 hours of growth.

Preparation of the HmGLUR3 DNA, Plasmid pSK-HmGluR3 and Plasmid pGTh-HmGluR3

The sequence of SEQ ID NO:1 was prepared from a human fetal brain cDNA library (commercially available from Stratagene, Inc., La Jolla, Calif. 92037, Catalogue #936206) with a complexity of $2 \times 10^6$. An aliquot of this library was used as a template with short synthetic oligonucleotide primers, designed by evaluation of the DNA sequences of the rat metabotropic receptors described in Tanabe, et al., Neuron, 8:169–172 (1992). Use of these oligonucleotides with the polymerase chain reaction generated a 0.9 kb DNA fragment. Using standard techniques, the DNA fragment was gel purified, radioactively labeled by PCR and used as a probe to screen the cDNA library for individual human HmGluR3 clones. Using standard plaque hybridization techniques (moderate stringency, 1 M Na+, 60° C.) a number of positive clones having homologous sequences were isolated. By further dilution and hybridization, a phage clone was purified which contained the complete human HmGluR3 sequence on a 3160 bp EcoRI fragment. The pBlueskript® phagemid containing the insert (see FIG. 1) was excised from the phage using helper phage and protocols supplied by Stratagene, Inc.

Figure 2:
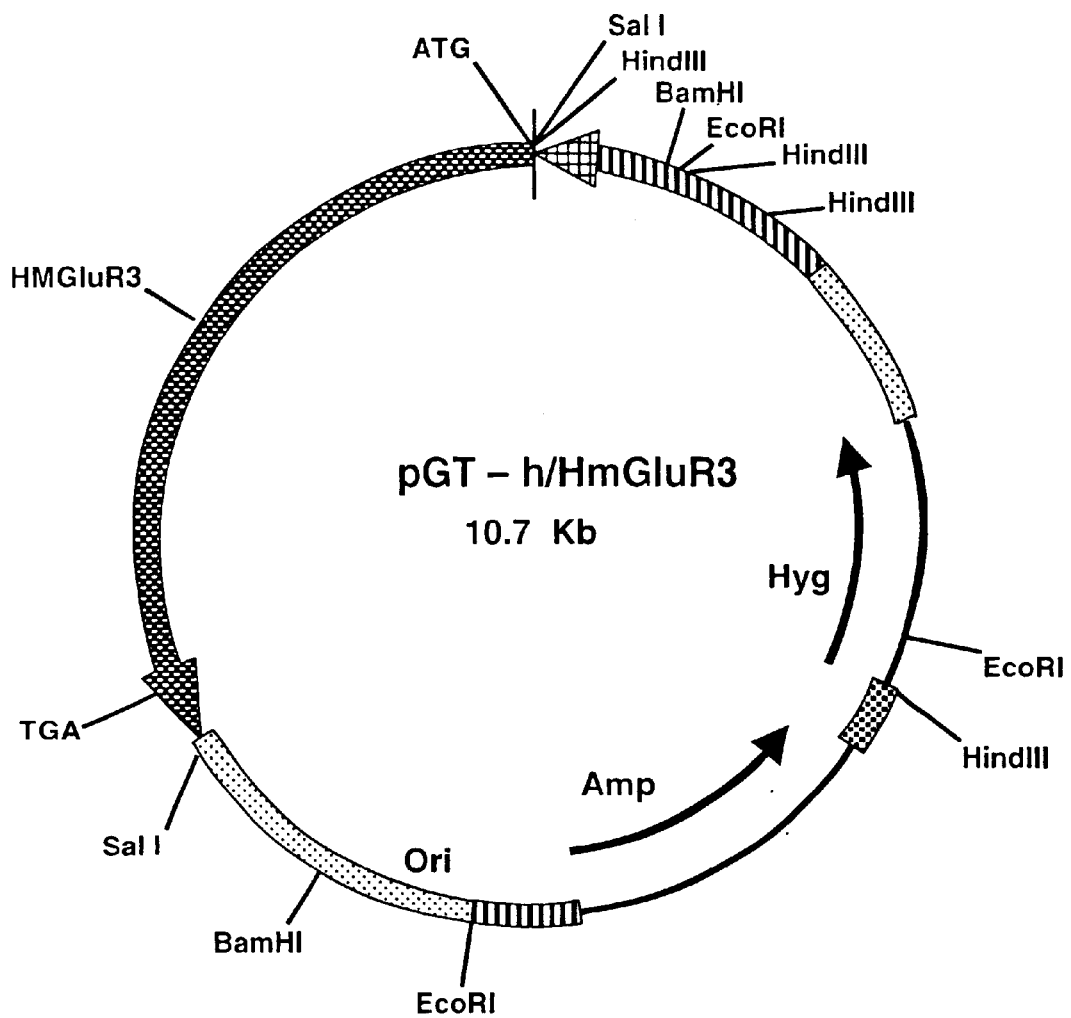
FIG. 2 is a restriction and function map of the plasmid pGTh/HmGluR3. The largest arc indicates that portion of the plasmid which corresponds to SEQ ID NO:1. The arrow delineates that region of the insert which encodes the protein of SEQ ID NO:2 with the direction of the arrow indicating the natural order of transcription from the 5' end to the 3' end. The designation "Ori" refers to the plasmid origin of replication.

After sequencing the entire insert it was determined that a cryptic ATG or methionine codon was present in the 5'-untranslated region (not depicted in SED ID NO:1) approximately 50 base pairs upstream of the true initiation codon. Using the Chameleons Double-Stranded, Site-Directed Mutagenesis Kit (commercially available from Stratagene, Inc., La Jolla, Calif. 92037, Catalog #200509) and two custom designed primers, the cryptic ATG was removed and replaced with a SalI restriction site. Simultaneously, the unique XbaI located in the polylinker was deleted and also replaced with a SalI restriction site. The coding sequence was removed from the resulting plasmid on a ~3 kb fragment and inserted into the mammalian expression vector pGTh (as described hereinbefore) which had been modified by replacing the BclI cloning site with a unique SalI site using commercially obtained linkers. Using standard techniques, the plasmid of ~10.7 kb was transfected into the RGT cell line by the calcium phosphate precipitation method (see Graham et al, supra) and selected for expression of hygromycin resistance. FIG. 2 shows the relative locations of the restriction sites and the direction of translation of the protein of the instant invention. Clones which expressed human HmGluR3 were identified by measuring agonist (t-ACPD) mediated inhibition of forskolin stimulated adenyl cyclase using a commercially available cAMP assay kit.

Adenylate Cyclase Activity

Adenylate cyclase activity was determined in initial experiments in transfected mammalian cells, using standard techniques. See. e.g., N. Adham, et al., supra,; R. L. Weinshank, et al., *Proceedings of the National Academy of Sciences (USA)*, 89:3630–3634 (1992), and the references cited therein.

As noted above, mammalian cells (the cell line RGT) were stably transfected with the plasmid pGTh-HmGluR3, containing human HmGluR3 cDNA inserted in the plasmid vector pGTh, as depicted in FIG. 2. The cells were maintained in a medium consisting of Dulbecco's Modified Eagle's Medium (DMEM) containing 5% dialyzed fetal calf serum, 10 mM HEPES buffer (pH 7.3), 1 mM sodium pyruvate, 1 mM glutamine, and 200 µg/ml hygromycin.

For the assay the cells were disassociated from stock culture flasks with trypsin, and planted in 24-well plastic culture dishes (15 mm wells) at a density of 500–700,000 cells per well using the same culture medium. After twenty four hours incubation in a humidified carbon dioxide incubator, the cell monolayers are washed with buffer (Dulbecco's phosphate-buffered saline containing 0.5 mM isobutylmethylxanthine and 3 mM glucose) and then incubated in the same buffer at 37° C. for 30 minutes. The monolayers are then washed four additional times with buffer.

Drugs and forskolin, or forskolin alone, dissolved in buffer, was added after the final wash. After incubating for 20 minutes at 37° C., 0.5 ml of 8 mM EDTA was added to each well. The plates were then placed in a boiling water bath for about four minutes. The supernatant fluids are then recovered from the wells and lyophilized. Cyclic adenosinemonophosphate (cAMP) determinations were carried out on the lyophilized samples using commercially available radioimmunoassay kits, following the manufacturer's instructions. The cAMP level in wells containing drug was compared to the forskolin controls. The results are shown in TABLE III below.

TABLE III

Potencies of Selected Agonists for HmGluR3 Expressed in RGT Cells

| Agonist | $EC_{50}$, µM |
|---|---|
| L-Glutamate | 5.38 |
| 1S,3R-1-aminocyclopentant-1,3-dicarboxylic acid (ACPD) | 2.23 |
| 2R,4R-4-aminopyrrolidine-2,4-dicarboxylate | 0.55 |
| L-2-(carboxycyclopropyl)glycine-I (L-CCG-I) | 0.012 |

What is claimed is:

1. An isolated nucleic acid encoding the human metabotropic glutamate receptor which comprises the amino acid sequence designated as SEQ ID NO:2.

2. A composition comprising an isolated nucleic acid containing a sequence encoding a human glutamate receptor as claimed in claim 1, wherein said sequence is selected from the group consisting of:
   a) SEQ ID NO:1
   b) SEQ ID NO:3
   c) a nucleic acid compound complementary to (a) or (b); and
   d) a fragment of (a), (b), or (c) that is at least 18 base pairs in length and which will selectively hybridize to human genomic DNA encoding a human metabotropic glutamate receptor.

3. The composition of claim 2 wherein the isolated nucleic acid is deoxyribonucleic acid.

4. The composition of claim 3 which is (a) or a sequence complementary to (a).

5. The composition of claim 3 which is pGTh/HmGluR3.

6. The composition of claim 2 wherein the isolated nucleic acid is ribonucleic acid.

7. The composition of claim 6 which is (b) or a fragment thereof.

8. An expression vector capable of producing a human metabotropic glutamate receptor or a fragment thereof in a host cell which comprises a nucleic acid as claimed in claim 2 in combination with regulatory elements necessary for expression of the nucleic acid in the host cell.

9. The expression vector of claim 8 for use in a host cell wherein the host cell is a mammalian cell line.

10. The expression vector of claim 9 which comprises a BK virus enhancer.

11. The expression vector of claim 10 which further comprises an adenovirus late promoter.

12. The expression vector of claim 11 wherein the mammalian cell line is the RGT cell line.

13. A transfected host cell harboring an expression vector as claimed in claim 8.

14. A transfected host cell as claimed in claim 13 which is a transfected mammalian cell line.

15. A transfected host cell as claimed in claim 14 which is RGT-18 transfected with pGTh/HmGluR3.

16. An isolated human metabotropic glutamate receptor which comprises the amino acid sequence designated herein SEQ ID NO:2.

17. A method for producing mGlur3 protein comprising the steps of:
   a) expressing a gene sequence identified herein as SEQ ID NO:1 in a suitable host cell such that a recombinant protein comprising SEQ ID NO:2 is expressed; and
   b) purifying said recombinant protein by any suitable method.

18. An mGlur3 protein produced by the method of claim 17.

* * * * *